United States Patent [19]
Hamill et al.

[11] Patent Number: 5,843,437
[45] Date of Patent: Dec. 1, 1998

[54] A82846 ANTIBIOTICS

[75] Inventors: Robert L. Hamill, Greenwood; James A. Mabe, Indianapolis; David F. Mahoney, Indianapolis; Walter M. Nakatsukasa, Indianapolis; Raymond C. Yao, Carmel, all of Ind.

[73] Assignee: Eli Lilly and Company, Indianapolis, Ind.

[21] Appl. No.: 466,656

[22] Filed: Jun. 6, 1995

Related U.S. Application Data

[60] Continuation of Ser. No. 147,358, Nov. 2, 1993, abandoned, which is a division of Ser. No. 521,202, May 9, 1990, Pat. No. 5,312,738, which is a continuation of Ser. No. 127,737, Dec. 2, 1987, abandoned, which is a continuation of Ser. No. 909,791, Sep. 19, 1986, abandoned.

[51] Int. Cl.$^6$ .............................. A61K 35/74; C12P 1/06; C12P 1/04
[52] U.S. Cl. ........................... 424/119; 435/169; 435/170
[58] Field of Search ............................ 424/119; 435/169, 435/170

[56] References Cited

U.S. PATENT DOCUMENTS

| | | | |
|---|---|---|---|
| 3,067,099 | 12/1962 | McCormick et al. | 167/65 |
| 4,547,488 | 10/1985 | Merkel | 514/10 |
| 4,548,924 | 10/1985 | Michel | 514/10 |
| 4,548,925 | 10/1985 | Higgins et al. | 514/10 |
| 4,558,008 | 12/1985 | Boeck et al. | 435/75 |
| 5,071,749 | 12/1991 | Kondo et al. | 514/10 |

FOREIGN PATENT DOCUMENTS 0 265 071  9/1987  European Pat. Off. .

OTHER PUBLICATIONS

A.H. Hunt, et al., "A51568A: N–Demethylvancomycin", *J. Antibiotics* 37(8), pp. 917–919 (Aug. 1984).

A.H. Hunt, "Structure of the Pseudaglycon of A35512B", *J. Am. Chem. Soc.* 105, pp. 4463–4468 (1983).

A.H. Hunt, et al., "Structure of Antibiotic A41030A", *J. Org. Chem.* 50, pp. 2031–2035 (1985).

A.H. Hunt, et al., "Structure of the Pseudoaglycon of Actaplanin", *J. Org. Chem.* 49, pp. 635–640 (1984).

A.H. Hunt, et al., "Structure of the Major Glycopeptide of the Teicoplanin Complex", *J. Am. Chem. Soc.* 106, pp. 4891–4895 (1984).

A.H. Hunt, et al., "Structures of the Actaplanins", *J. Org. Chem.* 49, pp. 641–645 (1984).

R.C. Yao, et al., "A82846, A New Glycopeptide Antibiotic Complex, producted by *Amycolatopsis orientalis*", *ICAAC Abstract No. 974ˆ*, p. 282 (23–26 Oct. 1988).

R.L. Hamill, et al., "A82846, A New Glycopeptide Complex, Produced by *Amycolaptosis orientalis*", *ICAAC Abstract No. 975*, p. 282 (23–26 Oct. 1988).

Ann H. Hunt, et al., "A82846, A New Glycopeptide Complex, Produced by *Amycolatopsis orientalis*", *ICAAC Abstract No. 976ˆ*, p. 282 (23–26 Oct. 1988).

F.T. Counter, et al., "A82846, A New Glycopeptide Complex, Produced by *Amycolatopsis orientalis*", *ICAAC Abstract No. 977*, p. 283 (23–26 Oct. 1988).

*Primary Examiner*—Jerome D. Goldberg
*Attorney, Agent, or Firm*—Kathleen R. S. Page; Janet T. McClain; David E. Boone

[57] ABSTRACT

New glycopeptide antibiotic A82846, comprising A82846A, A82846B and A82846C, is produced by *Nocardia orientalis* strains NRRL 18098, NRRL 18099 and NRRL 18100. The A82846 antibiotics have activity against Gram-positive bacteria comparable to that of vancomycin.

33 Claims, 9 Drawing Sheets

A82846 ANTIBIOTICS

This application is a continuation of application Ser. No. 08/147,358, filed on Nov. 2, 1993 now abandoned, which is a division of application Ser. No. 07/521,202, filed on May 9, 1990, now U.S. Pat. No. 5,312,738 which is a continuation of application Ser. No. 07/127,737, filed on Dec. 2, 1987, now abandoned, which is a continuation of application Ser. No. 06/909,791, filed on Sep. 19, 1986, now abandoned.

SUMMARY OF THE INVENTION

This invention relates to antibiotic A82846 comprising individual components A82846A, A82846B and A82846C and to their salts. Antibiotic A82846 is produced by culturing a new microorganism selected from *Nocardia orientalis* strains NRRL 18098, NRRL 18099, NRRL 18100 or an A82846-producing mutant, variant or recombinant thereof under submerged aerobic fermentation conditions.

The A82846 antibiotics inhibit the growth of certain pathogenic microorganisms, particularly Gram-positive microorganisms. The A82846 antibiotics also promote growth and improve feed efficiency in animals and improve milk production in ruminant animals.

This invention also relates to biologically-purified cultures of the *Nocardia orientalis* strains NRRL 18098, NRRL 18099 and NRRL 18100, which are useful for producing the A82846 antibiotics.

DESCRIPTION OF THE DRAWINGS

Infrared absorption spectra of the A82846 components are shown in FIGS. 1–3 as follows.

Figure 4:
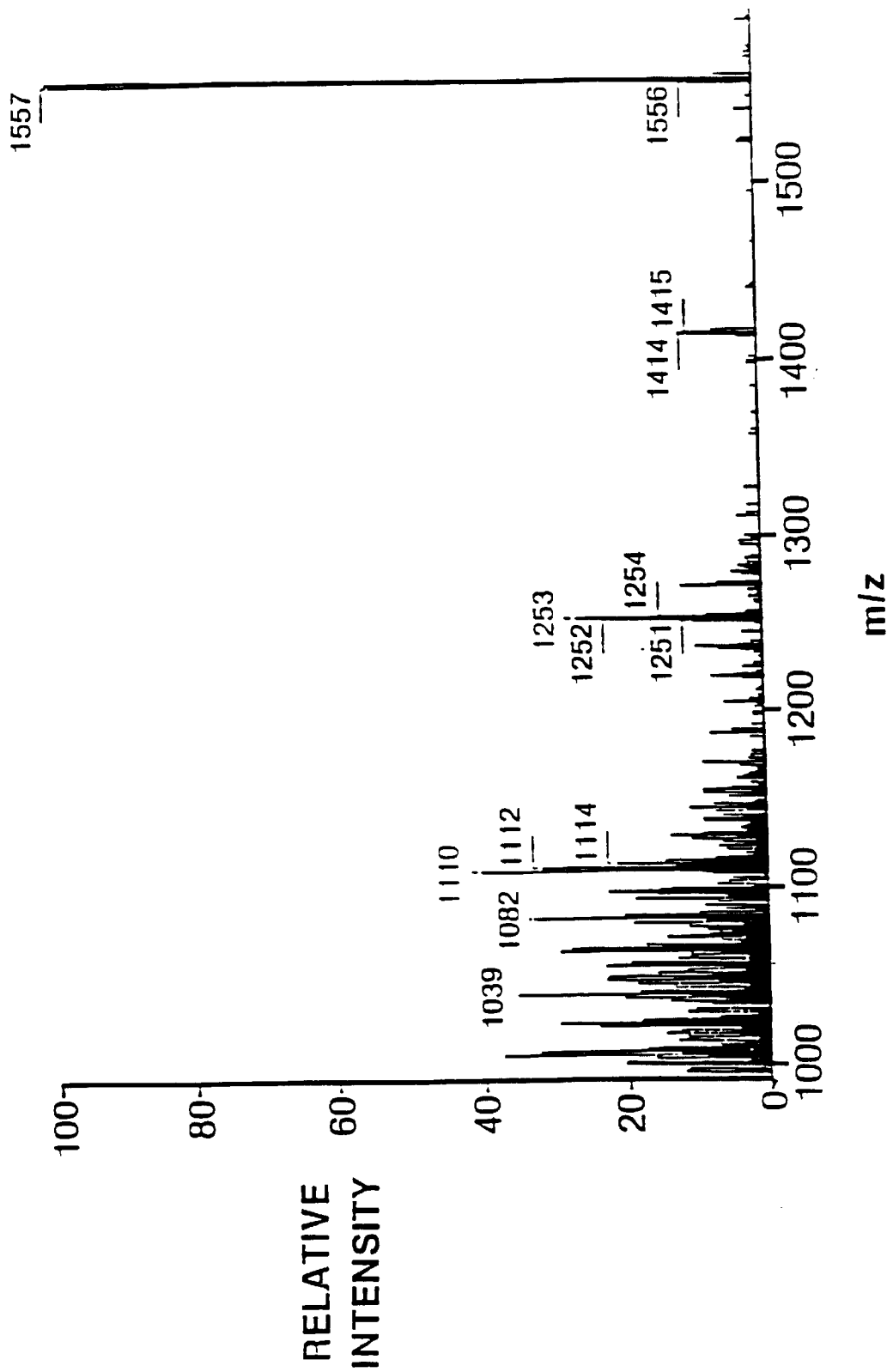
Figure 5:
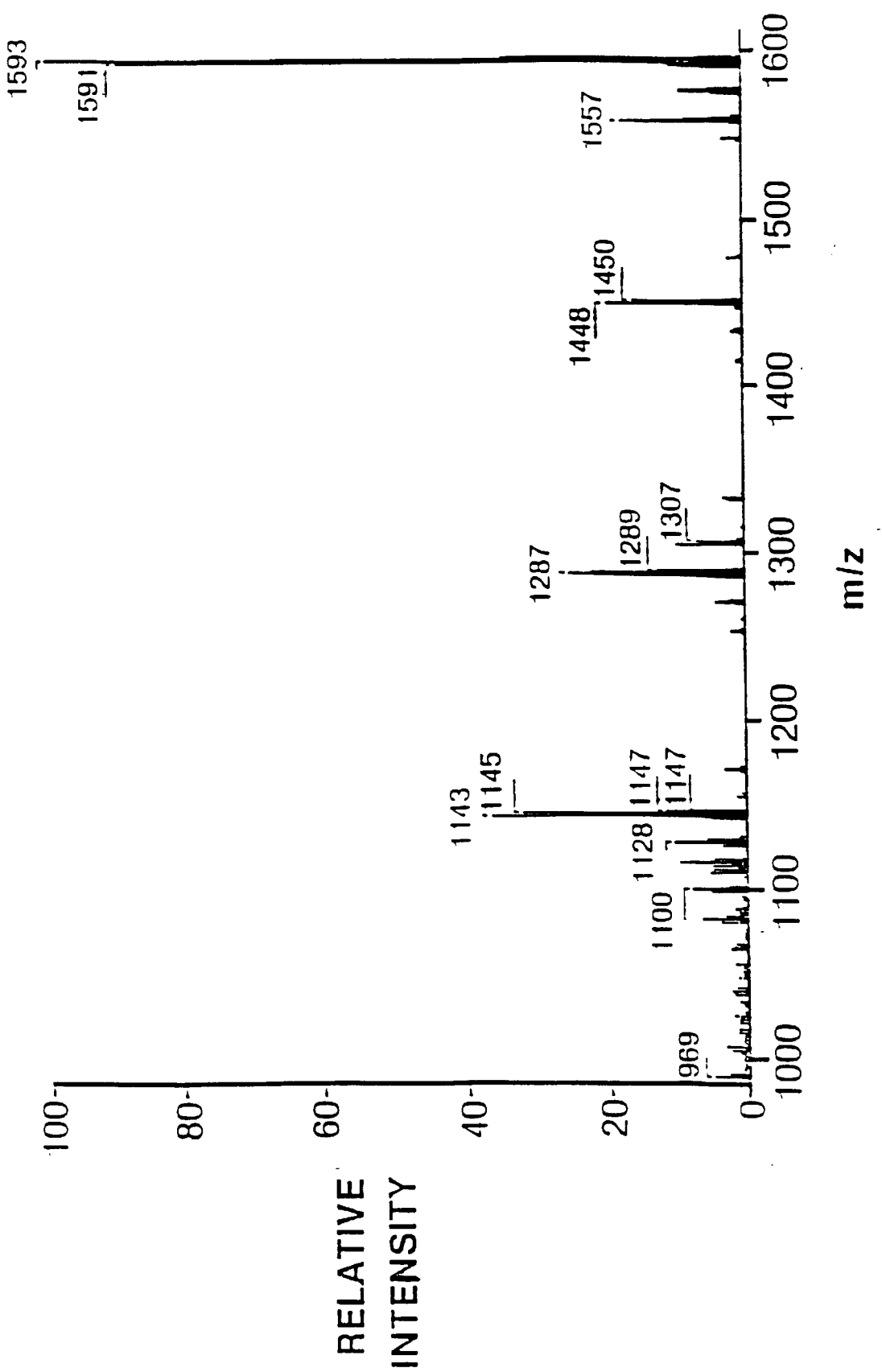
Figure 6:
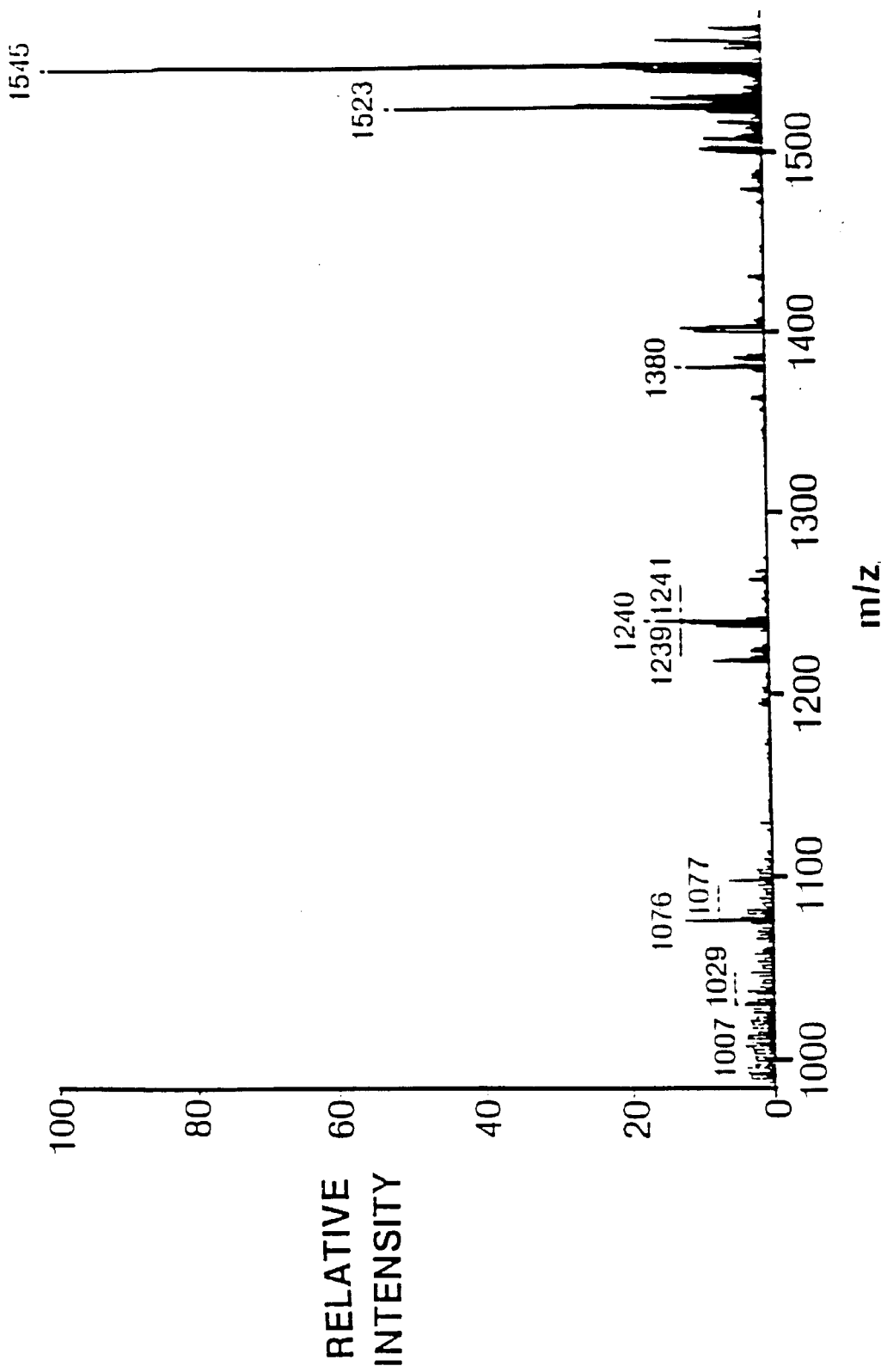
Figure 7:
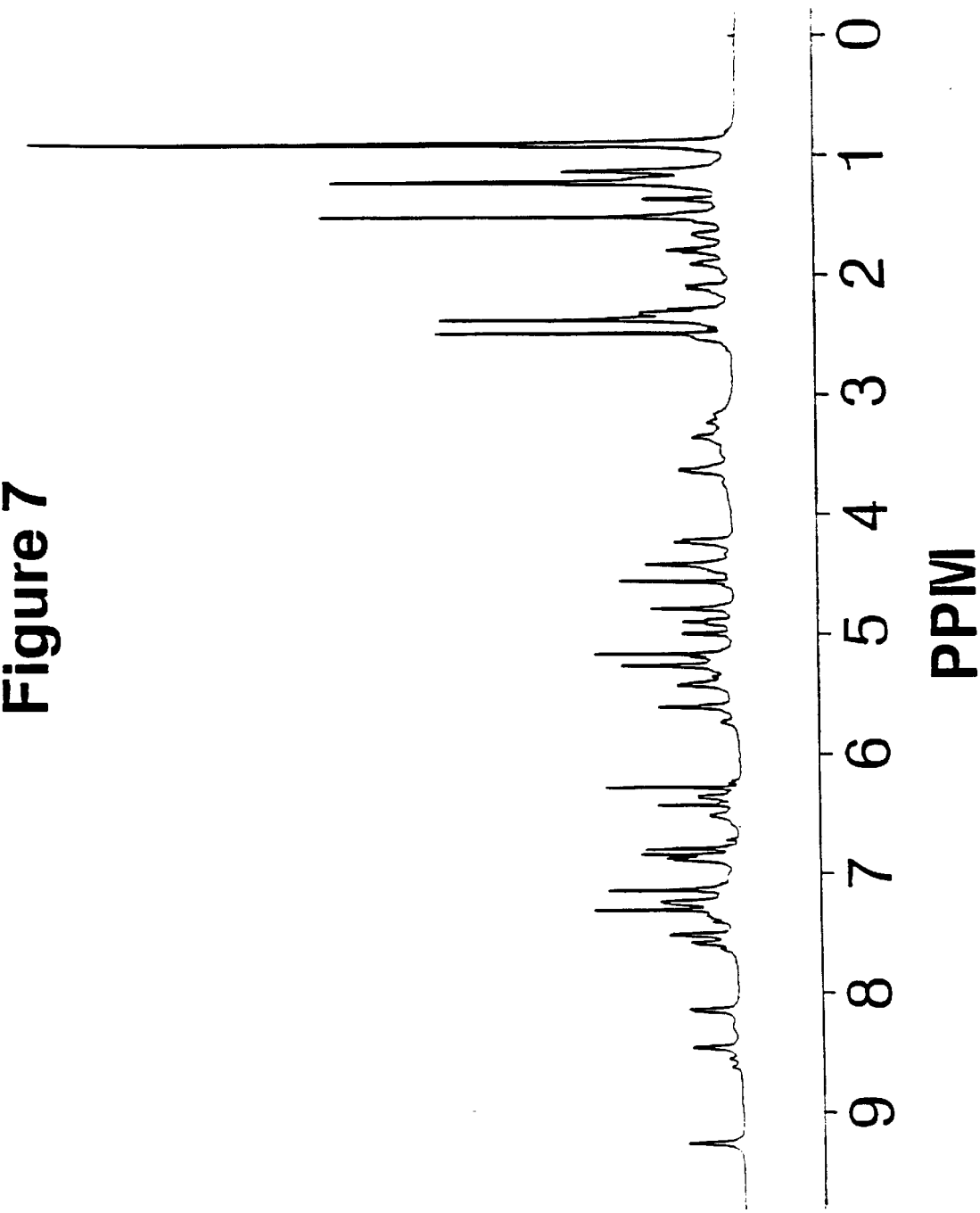
Figure 8:
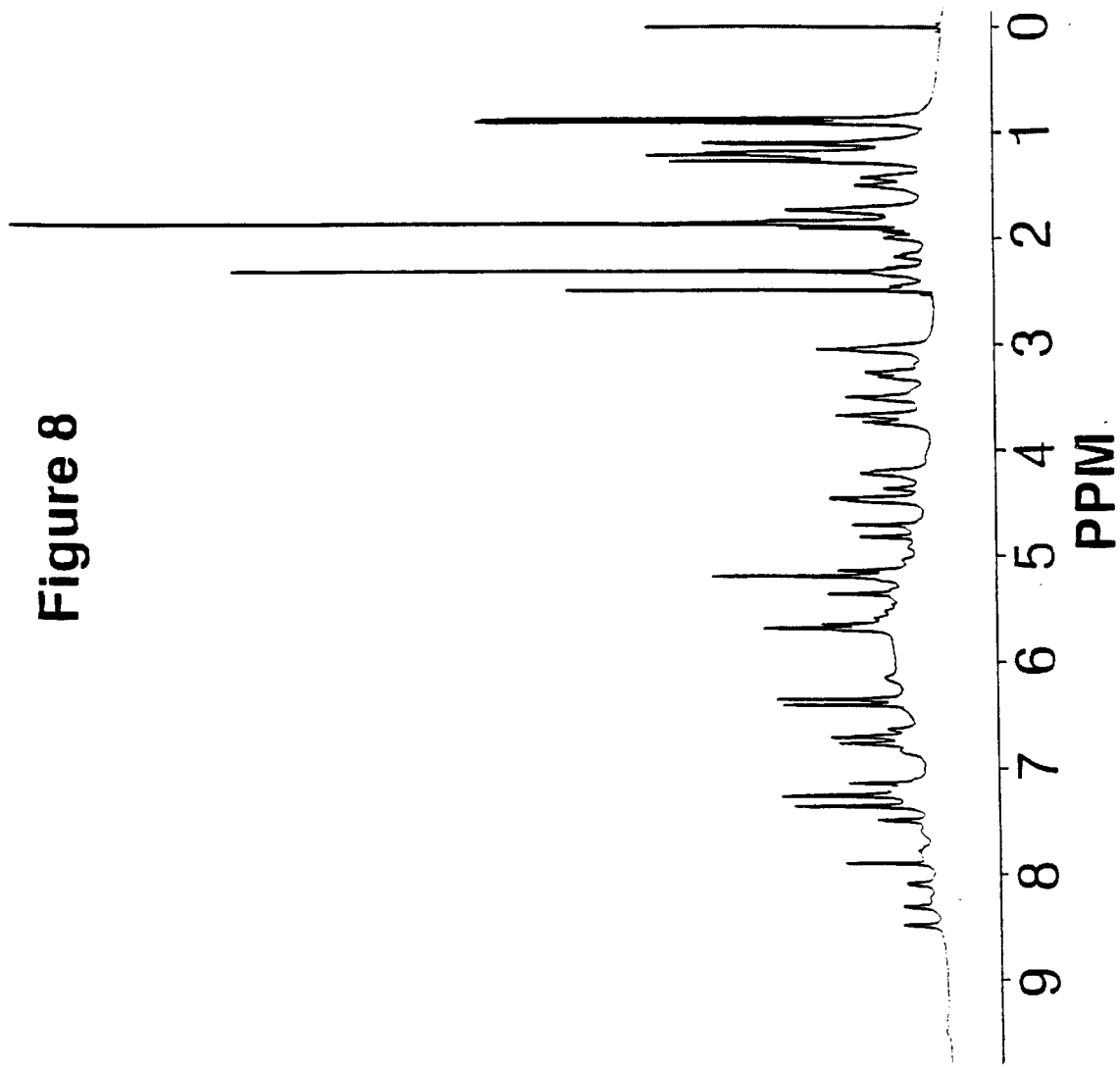
Figure 9:
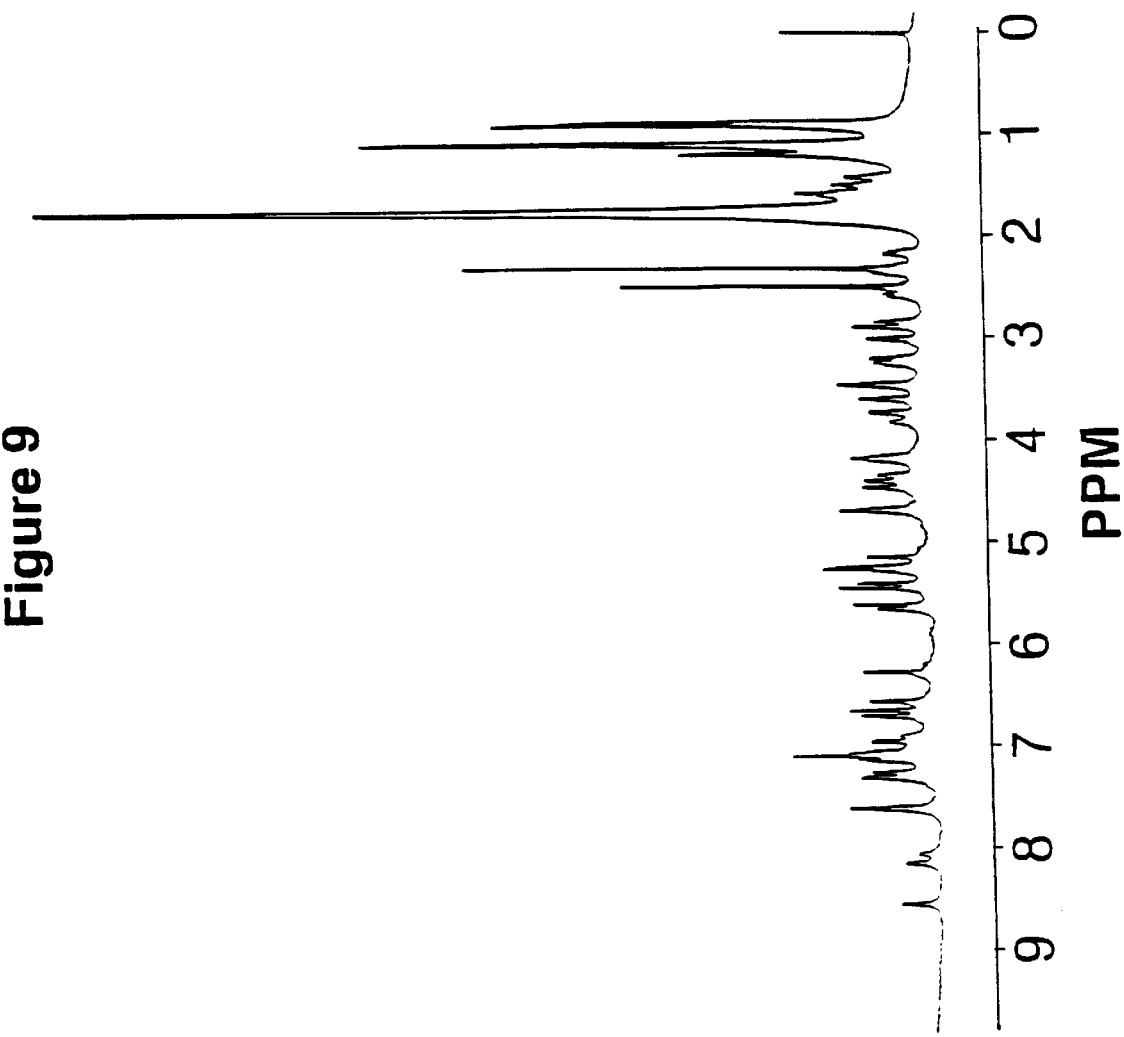

Fast-atom bombardment mass spectra (FAB-MS) of the A82846 components are shown in FIGS. 4–6 as follows:

Nuclear-magnetic-resonance (NMR) spectra of the A82846 components in (methyl sulfoxide)-$d_6$ at 60° on a Bruker AM500 spectrometer are shown in FIGS. 7–9 as follows:

FIG. 7—A82846A hydrochloride (HDO suppressed)

FIG. 8—A82846 B acetate

FIG. 9—A82846C acetate (HDO suppressed)

DETAILED DESCRIPTION OF THE INVENTION

Although many beneficial antibiotics are available today, the need to find improved antibiotics for human medicine continues. For example, vancomycin is a commercially successful antibiotic which has saved many lives. Vancomycin, however, can cause problems, e.g. it may cause ototoxicity and nephrotoxicity. Thus, antibiotics which have an activity like that of vancomycin but which have improved pharmacokinetics or fewer side effects are in demand.

This invention relates to an antibiotic which is structurally similar to vancomycin, but which has improved in vitro and in vivo activity against Gram-positive bacteria, as well as improved pharmacokinetics resulting in a much longer half-life than that of vancomycin. In particular, this invention relates to the new antibiotic A82846 comprising individual components A82846A, A82846B and A82846C, to the individual components and to their salts, especially their pharmaceutically acceptable salts.

Antibiotic A82846 is produced by culturing a novel microorganism selected from *Nocardia orientalis* NRRL 18098, *N. orientalis* NRRL 18099, *N. orientalis* 18100 or an A82846-producing mutant, variant or recombinant of these *N. orientalis* strains. As those skilled in fermentation processes will recognize, the ratio of the components in antibiotic A82846 will vary, depending upon the conditions used. A82846A, A82846B and A82846C are separated and isolated as individual compounds, as described infra.

In discussions of utility, the term "A82846 antibiotic" will denote a member selected from the group consisting of antibiotic A82846, A82846A, A82846B and A82846C and their pharmaceutically acceptable salts.

A82846 is soluble in water, dilute aqueous acid, dilute aqueous base and in mixtures of water and solvents such as methanol, ethanol, dimethylformamide, dimethyl sulfoxide, acetonitrile and acetone and the like.

The following paragraphs describe the physical and spectral properties of the A82846 components which have thus far been characterized.

A82846A

A82846A has the following characteristics:

Molecular Weight: 1556

Empirical Formula: $C_{73}H_{89}N_{10}O_{26}Cl$

FAB-MS (thioglycerol): (M+1) Found: 1557.5803; Calcd. $C_{73}H_{90}N_{10}O_{26}Cl=1557.5716$ (see FIG. 4)

UV ($H_2O$) $\lambda$max: 281 nm ($\epsilon$ 5,052), shifts to 300 nm with base

Figure 1:
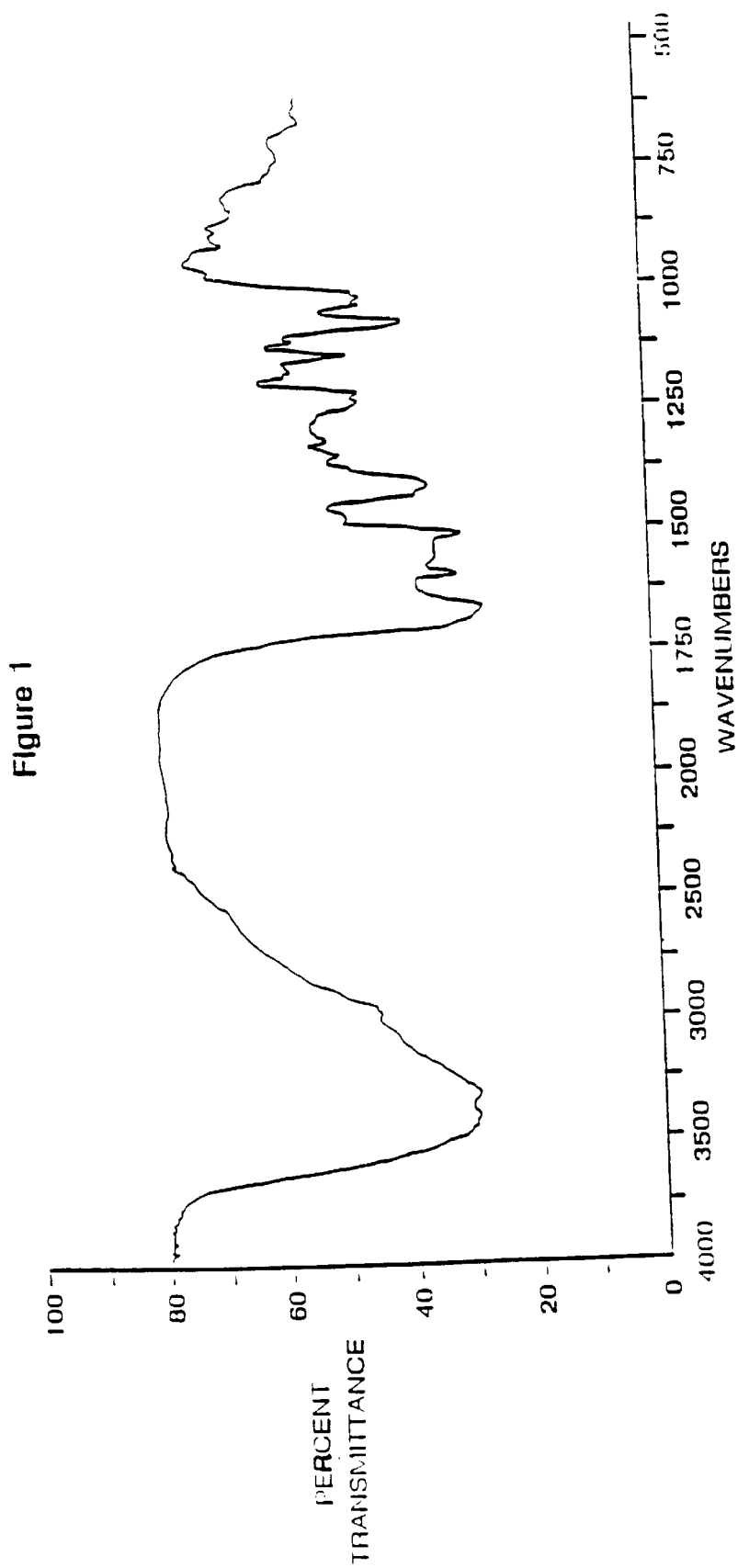
FIG. 1—A82846A (in KBr disk)

IR (KBr): 1716, 1655, 1611, 1586, 1552, 1504, 1410, 1340, 1310, 1230, 1212, 1132, 1066, 1028 and 1015 $cm^{-1}$ (see FIG. 1)

NMR [$(CD_3)_2SO$]: see FIG. 7 pKa ($H_2O$): 4.7, 9.5

(66% DMF): 5.5, 6.8, 7.9, 9.4, 12.3 (apparent mol. wt. 1542)

A82846B

A82846B has the following characteristics:

Molecular Weight: 1590

Empirical Formula: $C_{73}H_{88}N_{10}O_{26}Cl_2$

FAB-MS (thioglycerol): (M+1) Found: 1591.5315; Calcd. $C_{73}H_{89}N_{10}O_{26}Cl_2=1591.5327$ (see FIG. 5)

UV ($H_2O$) $\lambda$max: 280 nm ($\epsilon$ 5,192), shifts to 300 nm with base

Figure 2:
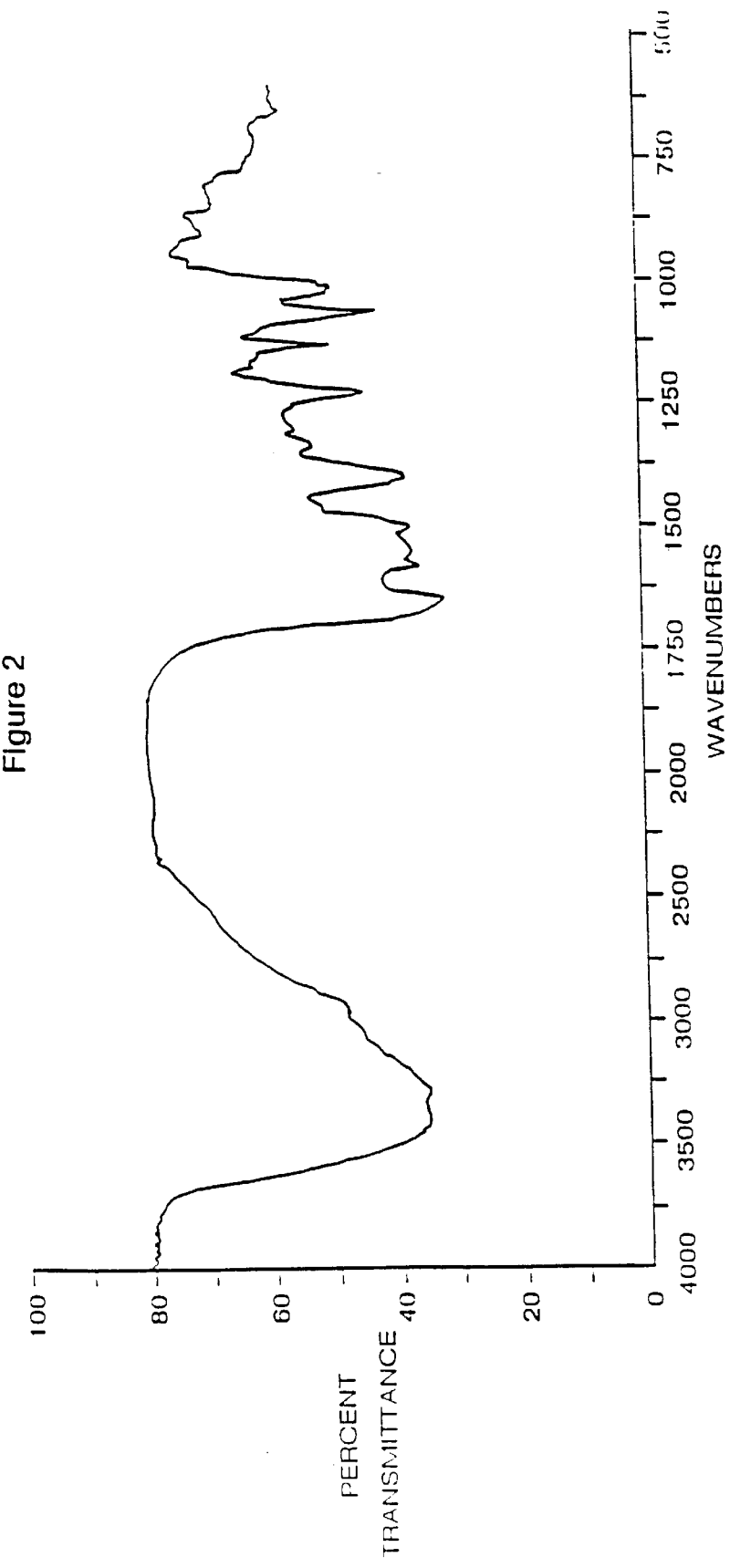
FIG. 2—A82846B (in KBr disk)

IR (KBr): 1656, 1586, 1562, 1504, 1403, 1264, 1230, 1135, 1105, 1065, 1023, and 1018 $cm^{-1}$ (see FIG. 2)

NMR [$(CD_3)_2SO$]: see FIG. 8 pKa ($H_2O$): 4.65, 9.5

A82846C

A82846C has the following characteristics:

Molecular Weight: 1522

Empirical Formula: $C_{73}H_{90}N_{10}O_{26}$

FAB-MS (thioglycerol): (M+Na) Found: 1545.5998; calcd. $C_{73}H_{90}N_{10}O_{26}Na=1545.5925$ (see FIG. 6)

UV ($H_2O$) $\lambda$max: 280 nm ($\epsilon$ 5,198), shifts to 300 nm with base

Figure 3:
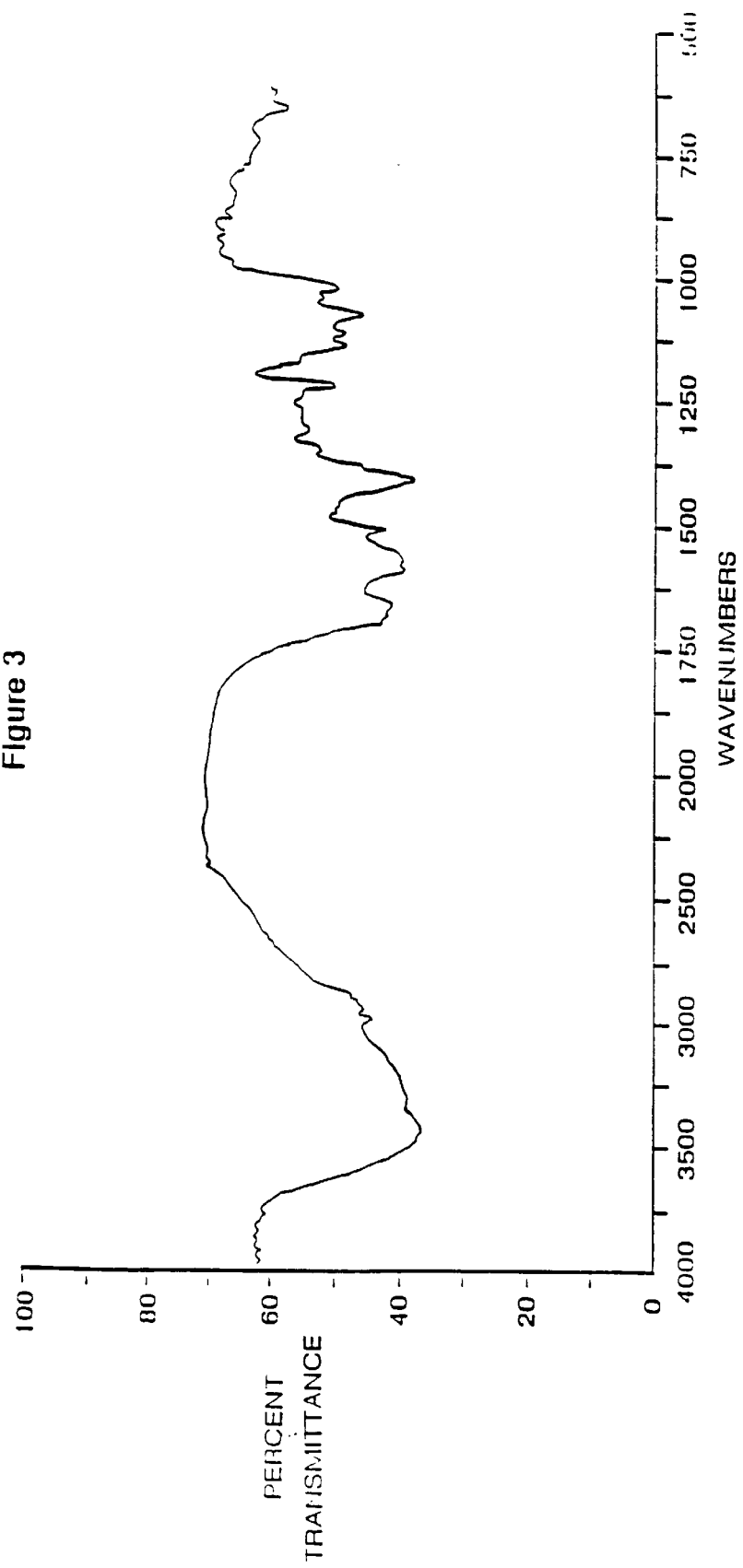
FIG. 3—A82846C (in KBr disk)

IR (KBr): 3600→3004 (broad), 2999, 2991, 2950, 1687→1650, (broad), 1585, 1570, 1509, 1503, 1453, 1449, 1402, 1212, 1130, 1102, 1060, 1032 and 1014 cm$^{-1}$ (see FIG. 3)

NMR [(CD$_3$)$_2$SO]: see FIG. 9 pKa (H$_2$O): 4.6, 9.4

Amino acid analyses of A82846A, A82846B and A82846C, after hydrolysis with 6N HCl, indicated the presence of aspartic acid and two broad peaks with a trace of glycine. The two peaks appear to correspond to actinoidinic and vancomycinic amino acids, both of which are present in glycopeptides of the vancomycin class.

Comparative NMR studies indicate that A82846A, A82846B and A82846C each contain the novel amino-sugar 4-epi-vancosamine (3-methyl-acosamine):

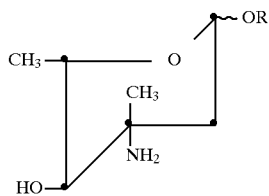

The molecular formula of A82846A corresponds to that of vancomycin (C$_{66}$H$_{75}$N$_9$O$_{24}$Cl$_2$) minus one chlorine atom plus the elements of an additional amino sugar of the vancosamine type (C$_7$H$_{14}$NO$_2$).

The molecular formula of A82846B corresponds to that of A82846A in which a hydrogen atom is replaced by a chlorine atom.

The molecular formula of A82846C corresponds to that of A82846A in which a chlorine atom has been replaced by hydrogen.

Thus, the A82846 components appear to constitute a new family of glycopeptides which clearly resemble the vancomycin molecule in general composition, differing mainly in chlorine content and in the presence of an additional subunit having a vancosamine composition.

A82846 and its individual components A82846A, A82846B and A82846C can react to form various salts. All such forms of these antibiotics are part of this invention. A82846 salts are useful, for example, for separating and purifying A82846. In addition, the salts have an improved solubility in water.

A82846 salts are prepared using standard procedures for salt preparation. For example, A82846 can be neutralized with an appropriate acid to form an acid addition salt.

The acid addition salts are particularly useful. Representative suitable salts include those salts formed by standard reactions with both organic and inorganic acids such as, for example, sulfuric, hydrochloric, phosphoric, acetic, succinic, citric, lactic, maleic, fumaric, cholic, pamoic, mucic, D-glutamic, d-camphoric, glutaric, glycolic, phthalic, tartaric, formic, lauric, stearic, salicylic, methanesulfonic, benzenesulfonic, sorbic, picric, benzoic, cinnamic and like acids.

Pharmaceutically acceptable acid addition salts are an especially preferred group of salts of this invention.

Antibiotic A82846 is produced by culturing an A82846-producing strain of *Nocardia orientalis* under submerged aerobic conditions in a suitable culture medium until substantial antibiotic activity is produced. The antibiotic can be recovered using various isolation and purification procedures understood in the art.

This invention also relates to a biologically-purified culture of a microorganism selected from *Nocardia orientalis* NRRL 18098, *Nocardia orientalis* NRRL 18099, *Nocardia orientalis* NRRL 18100 or an A82846-producing mutant, variant or recombinant of these strains. These microorganisms are useful because they produce antibiotic A82846. For convenience in the discussion which follows, the NRRL 18098 strain has been designated culture A82846, the NRRL 18099 strain has been designated culture A82846.1 and the NRRL 18100 strain has been designated culture A82846.2. Culture A82846 was isolated from a soil sample from Haiti. Culture A82846.1 was obtained from culture A82846 by chemical mutagenesis, and culture A82846.2 is a natural variant isolated from culture A82846.

Cultures A82846, A82846.1 and A82846.2 have been deposited and made part of the stock culture collection of the Midwest Area Northern Regional Research Center, Agricultural Research Service, United States Department of Agriculture, 1815 North University Street, Peoria, Ill., 61604, from which they are available to the public under the accession numbers NRRL 18098 (A82846, the parent strain), NRRL 18099 (A82846.1, the mutant strain) and NRRL 18100 (A82846.2, the variant strain).

Taxonomic studies of cultures A82846, A82846.1 and A82846.2 were carried out by Frederick P. Mertz of the Lilly Research Laboratories. Based on these studies, the new organisms are classified as strains of *Nocardia orientalis* (Pittenger and Brigham, 1956) Pridham and Lyons 1969, type strain: ATCC 19795 [R. C. Pittenger and R. B. Brigham, "*Streptomyces orientalis* n. sp., the Source of Vancomycin," *Antibiotics and Chemotherapy* 6, 642–647 (1956)]. This classification is based on direct laboratory comparisons and examination of published descriptions [*Bergey's Manual of Determinative Bacteriology*, 8th ed., R. E. Buchanan and N. E. Gibbons, Eds., The Williams and Wilkins Co., Baltimore, 1974; M. Goodfellow and K. P. Schaal, "Identification Methods for Nocardia, Actinomadura and Rhodococcus", in *Identification Methods for Microbiologists*, 2nd ed., F. A. Skinner and D. W. Lovelock, Eds., Society for Applied Bacteriology Technical Series No. 14, Academic Press, Inc., New York, 1979, p. 261; R. E. Gordon, D. A. Barnett, J. E. Handerhan and C. H. Pang, "*Nocardia coeliaca*, *Nocardia autotrophica*, and the Nocardin Strain", *Int. J. Syst. Bacteriol.* 24(1), 54–63 (1974); R. E. Gordon, S. K. Mishra and D. A. Barnett, "Some Bits and Pieces of the Genus Nocardia: *N. carnea, N. vaccinii, N. transvalensis, N. orientalis*, and *N. aerocolonigenes*", *J. Gen. Microbiol.* 109, 69–78 (1978); S. J. Mishra, R. E. Gordon, and D. A. Barnett, "Identification of Nocardiae and Streptomyces of Medical Importance", *J. Clin. Microbiol.* 11(6), 728–736 (1980); H. Mordarska and M. Mordarski, "Chemotaxonomic Characters and Classification of Some Nocardioform Bacteria", *J. Gen. Microbiology* 71, 77–86 (1972); and R. Shinobu and M. Kawato, "On *Streptomyces aerocolonigenes* nov. sp., Forming the Secondary Colonies on the Aerial Mycelia," *Bot. Mag. Tokyo* 73, 213–216 (1960)].

Methods Used

The methods followed were those recommended by the International Streptomyces Project (ISP) for the characterization of Streptomyces species [E. B. Shirling and D. Gottlieb, "Methods for Characterization of Streptomyces Species," *Int. J. Syst. Bacteriol.* 16:313–340 (1966)] and those recommended for the characterization of Nocardia species by Gordon, Barnett, Handerhan and Pang, supra.

Morphology was studied using an optical light microscope. A scanning electron microscope (SEM) was used to study the spore surface ornamentation.

Resistance to rifampin and lysozyme was measured by methods recommended by Gordon [R. E. Gordon and D. A. Barnett, "Resistance to Rifampin and Lysozyme of Strains of Some Species of Mycobacterium and Nocardia as a Taxonomic Tool," *Int. J. Syst. Bacteriol.* 27(3), 176–178 (1977)].

ISCC-NBS Centroid Color Charts, standard sample No. 2106 (National Bureau of Standards, 1958, U.S. Department of Commerce, Washington, D.C.) and the *Color Harmony Manual* (4th ed., Container Corporation of America, Chicago, Ill., 1958) were used to assign color names.

Melanoid pigment production (chromogenicity) was determined with ISP No. 1 (tryptone-yeast extract broth), ISP No. 6 (peptone-yeast extract iron agar) and ISP No. 7 (tyrosine agar) media.

The isomers of diaminopimelic acid (DAP) and the carbohydrates in hydrolysates of whole cells were established by the chromatographic methods of Becker et al. [B. Becker, M. P. Lechevalier, R. E. Gordon and H. A. Lechevalier, "Rapid Differentiation between Nocardia and Streptomyces by Paper Chromatography of Whole-cell Hydrolysates," *Appl. Microbiol.* 12, 421–423 (1964)] and of Lechevalier [M. P. Lechevalier, "Identification of Aerobic Actinomycetes of Clinical Importance," *J. Lab. Clin. Med.* 71, 934–944 (1968)].

Mycolic acids were determined by a method based on techniques described by Minnikin [D. E. Minnikin, I. G. Hutchinson and A. B. Caldicott, "Thin-Layer Chromatography of Methanolysates of Mycolic Acid-Containing Bacteria," *J. Chromatography* 188, 221–233 (1980)].

Phosphatase and urease were determined by methods described by Blazevic, (D. J. Blazevic and G. M. Ederer, *Principles of Biochemical Tests in Diagnostic Microbiology*, John Wiley and Sons, Inc., New York, 1975, p. 136). Gelatin liquefaction was used to determine proteinase activity.

Resistance to antibiotics was measured by padding antibiotic sensitivity discs onto the surface of seeded ISP No. 2 agar plates.

Starch hydrolysis was determined by testing for the presence of starch with iodine on ISP No. 4 (inorganic salts-starch) agar plates (See Blazevic and Ederer, supra).

Hippurate hydrolysis was measured by using Bacto Differentiation Disks which rapidly detect the hydrolysis of hippurate.

Cultural Characteristics

Cultures A82846 and A82846.2 grew well on all the complex and defined media used. These cultures produced aerial mycelia on most media. The color of the aerial spore mass was white or gray, depending on the medium. A distinctive brown soluble pigment was produced on many media; the reverse side was brown to yellowish white.

Culture A82846.1 also grew on all the media used but its growth was less abundant than that of the parent. A82846.1 produced aerial mycelia only rarely. When present, the mycelial color was white. An occasional non-distinctive light brown soluble pigment was produced on a few media; the reverse side was brown to yellowish white.

The cultural characteristics of cultures A82846, A82846.1 and A82846.2 are summarized in Table I. Cultures A82846 and A82846.2 were very similar, differing in only a few cultural properties. Because of their similarity and since A82846.2 is a natural variant of A82846, no further comparisons were made.

TABLE I

Cultural Characteristics of A82846, A84846.1 and A82846.2 on Various Agar Media[a,b]

| Agar Media | | A82846 | A82846.1 | A82846.2 |
|---|---|---|---|---|
| ISP No. 2 | G: | Abundant | Abundant (surface peel off) | Abundant |
| | R: | 59.d.Br | 57.1.Br | 58.m.Br |
| | Am: | Abundant:g Medium Gray | None | Trace |
| | Sp: | Dark brown pigment - no pH change | None | Light brown |
| ISP No. 3 | G: | Good | Poor | Good |
| | R: | 92.y White | 92.y White | 92.y white |
| | Am: | Good:a White | Poor:a White | Fair:a white |
| | SP: | None | None | None |
| ISP No. 4 | G: | Abundant | Poor | Good |
| | R: | 56 deep Br | 92.y White | 77.m.y Br |
| | Am: | Abundant:a White | Poor:a White | Good:a white |
| | SP: | None | None | None |
| ISP No. 5 | G: | Abundant | Abundant | Abundant |
| | R: | 47.d.gy.rBr | 47.d.gy.rBr | 47.d. gy. rBr |
| | Am: | Good:d Light gray | None | Good:d light gray |
| | Sp: | Light brown | Light brown | Light brown |
| ISP No. 7 | G: | Abundant | Good | Abundant |
| | R: | 59.d.Br | 78.d.yBr | 59.d.Br |
| | Am: | Abundant:e Medium gray | Trace | Abundant:d Light gray |
| | Sp: | Dark brown pigment - no pH change | Light brown pigment | Dark brown pigment |
| Czapek's | G: | Abundant | Good | Abundant |
| | R: | 56.deep Br | 47.d.gy.rBr | 5b. deep Br |
| | Am: | Abundant:a White | None | Abundant:a White |
| | Sp: | None | Reddish-orange | Light reddish-orange |
| Glucose Asparagine | G: | Good | Good | Good |
| | R: | 58.m.Br (patches only) | 77.m.yBr | 58.m.Br |
| | Am: | Fair: A White | None | None |
| | Sp: | None | None | None |
| | G: | Abundant (surface peel off) | Good (wrinkled, moist | Good (wrinkled, moist |

TABLE I-continued

Cultural Characteristics of A82846, A84846.1 and A82846.2 on Various Agar Media[a,b]

| Agar Media | | A82846 | A82846.1 | A82846.2 |
|---|---|---|---|---|
| | | | surface) | surface) |
| Glucose | R: | 21.blackish red | 77.m.yBr | 77.m.yBr |
| Yeast | Am: | None | None | None |
| Extract | Sp: | Deep reddish brown | None | Light Brown |
| | G: | Good | Good | Fair |
| Nutrient | R: | 45.1.gy.rBr | 76.1.yBr | 79.1.9y.yBr |
| Agar | Am: | None | None | Poor |
| | Sp: | Light brown | None | None |
| | G: | Abundant | Abundant | Abundant |
| Tomato | R: | 47.d.gy.rBr | 57.1.Br | 47.d.9y.rBr |
| Paste | Am: | Abundant:d Light gray | Trace:a White | Good:d Light gray |
| Oatmeal | Sp: | Dark reddish brown | None | Reddish brown |
| | G: | Fair | Fair | Good |
| Tap | R: | 92.y White | 92.y White | 92.y White |
| Water | Ain: | Fair:a White | Fair: b Oyster White | Good:a White |
| Agar | Sp: | None | None | None |
| | G: | Fair (no hydrolysis) | Good (hydrolysis) | Fair (no hydrolysis) |
| Calcium | R: | 57.1.Br | 58.m.Br | 57.1.Br |
| Malate | Arn: | Trace | None | Trace |
| | Sp: | Light brown | Light brown | Light brown |

[a]G = growth;
R = reverse;
Am = aerial mycelium;
Sp = soluble pigment
[b]Incubated at 30° C. for 21 days

Morphological Characteristics

Cultures A82846, A82846.1 and A82846.2 produced an extensive substrate mycelium. Aerial hyphae formed long chains of conidia with a cobweb appearance which is classified as characteristic of nonstreptomycetes in *Bergey's Manual of Determinative Bacteriology*, supra.

In all cultures the spore-surface ornamentation was smooth and spore shape was cylindrical. The spore size ranged from 1.2–1.3×0.4–0.5 $\mu$M for A82846 and 1.4–2.2× 0.3–0.4 $\mu$M for A82846.1.

When grown under submerged shaken conditions, A82846 exhibited minimal fragmentation, A82846.1 fragmented extensively and A82846 exhibited moderate fragmentation.

Physiological Characteristics

Cultures A82846 and 82846.1 both produced acid from: arabinose, cellobiose, dextran, fructose, galactose, glucose, α-methyl-D-glucoside, glycerol, inositol, lactose, maltose, mannitol, mannose, melibiose, rhamnose, ribose, sucrose, trehalose and xylose, but did not produce acid from adonitol, cellulose, dulcitol, erythritol, inulin, sorbitol and xylitol. A82846 also produced acid from: ethanol, glycogen, melezitose, raffinose and salicin, but A82846.1 did not. Both cultures used acetate, citrate, lactate, malate, oxalate, propionate, pyruvate and succinate, but did not use benzoate, mucate and tartrate. Culture A82846.1 utilized butyrate, but A82846 did not.

A82846 and A82846.1 decomposed casein, hypoxanthine, tyrosine, urea and DNA, but did not decompose adenine, calcium malate or xanthine. Both cultures hydrolyzed starch, did not hydrolyze esculin or hippurate, reduced nitrate, liquefied gelatin, survived 50° C. for 8 hours and produced catalase, H$_2$S and phosphatase.

Cultures A82846 and A82846.1 had identical antibiotic resistance patterns. They were resistant to bacitracin (10 units), cephalothin (30 $\mu$g), gentamicin (10 $\mu$g), lincomycin (2 $\mu$g), oleandomycin (15 $\mu$g), penicillin G (10 units), streptomycin (10 $\mu$g), vancomycin (30 $\mu$g), tobramycin (10 $\mu$g), erythromycin (15 $\mu$g), nalidixic acid (30 $\mu$g), polymixin B (300 units), trimethoprim (5 $\mu$g) and sulfadiazine (300 $\mu$g), and were sensitive to neomycin (30 $\mu$g), rifampin (5 $\mu$g), tetracycline (30 $\mu$g), chloramphenicol (30 $\mu$g), novobiocin (30 $\mu$g), and mandelamine (3 $\mu$g).

A82846 and A82846.1 each stained Gram+but did not stain acid fast. A82846 produced melanoid pigments, whereas A82846.1 did not.

Cell-Wall Analysis

Hydrolyzed whole cells of A82846 contained the meso isomer of diaminopimelic acid and the sugars arabinose and galactose. The cultures have a Type IV cell wall, according to Becker et al., supra. The sugar pattern is Type A (Lechavalier, supra). The cultures did not produce mycolic acids (LCN-A).

Identity of Strain A82846

The chemotaxonomic and general cultural characteristics of strain A82846 are consistent with its assignment to the genus Nocardia Trevisan 1889 [V. B. D. Skerman, V. McGowan and P. H. A. Sneath, Eds., "Approved Lists of Bacterial Names", *Int. J. Syst. Bacteriol.* 30, 225–420 (1980)].

Similarity coefficients were calculated from properties of fourteen Nocardia species published by Gordon, Mishra and Barnett, supra, and five strains from the Lilly culture collection. The coefficient of Jaccard [see P. H. A. Sneath, "The Application of Computers to Taxonomy", *J. Gen. Microbiol.* 17, 201 (1957)] and the simple matching coefficient [see R. R. Sokal and C. D. Michener, "A Statistical Method for Evaluating Systematic Relationships", *Kan. Univ. Sci. Bull.* 38, 1409 (1958)] were used. The results of these comparisons are summarized in Table II.

TABLE II

Similarity Coefficients for A82846 and 19 Other Nocardia Species

| Culture | Similarity Coefficient Ssm | Sj |
|---|---|---|
| A82846 | 100 | 100 |
| N. aerocolonigenes | 84 | 76 |
| N. aerocolonigenes (A42125)* | 83 | 78 |
| N. orientalis (M43-05865) | 78 | 72 |
| N. orientalis (A51568.1) | 78 | 72 |
| N. orientalis | 75 | 68 |
| N. orientalis (M5-18215) | 73 | 66 |
| N. orientalis (M5-18260) | 73 | 66 |
| N. madurae | 73 | 63 |
| N. hirsuta | 62 | 60 |
| N. autotrophica | 62 | 53 |
| N. dassonvillei | 62 | 50 |
| N. amarae | 62 | 46 |
| N. brasiliensis | 56 | 43 |
| N. vaccinci | 56 | 43 |
| N. transvalensis | 48 | 38 |
| N. caviae | 48 | 32 |
| N. pelletieri | 48 | 24 |
| N. asteroides | 46 | 23 |
| N. carnea | 43 | 25 |

*Numbers in parentheses indicate strains from the Lilly culture collection.

Because N. madurae has been transferred to the genus Actinomadura, it was removed from consideration. Two species, N. aerocolonigenes and N. orientalis, had good similarity coefficients. Laboratory comparisons between A82846 and these two species were made. Table III gives the results of these comparisons.

TABLE III

Comparison of Properties of A82846, N. orientalis and N. aerocolonigenes

| Property | 82846 | N. orientalis | N. aerocolonigenes |
|---|---|---|---|
| Produces aerial hyphae | + | + | + |
| Aerial color white | + | + | + |
| Produces Conidia | + | + | + |
| Spore surface smooth | + | + | + |
| Spore shape cylindrical | + | + | − |
| Produces soluble pigment | + | − | − |
| Gram + | + | + | + |
| Acid fast | − | − | − |
| Exhibits fragmentation | + | + | + |
| Produces catalase | + | + | + |
| Hydrolyzes: | | | |
| esculin | − | + | + |
| hippurate | − | − | − |
| starch | + | + | + |
| Ca malate | − | + | + |
| Reduces nitrate | + | + | − |
| Decomposes: | | | |
| adenine | − | − | − |
| casein | + | + | + |
| hypoxanthine | + | + | + |
| tyrosine | + | + | + |
| urea | + | + | + |
| xanthine | − | − | − |
| Liquefies gelatin | + | + | − |
| Produces phosphatase | + | + | + |
| Survives at 50° C., 8 h | + | + | − |
| Produces acid from: | | | |
| adonitol | − | + | − |
| arabinose | + | + | + |
| cellobiose | + | + | + |
| erythritol | − | + | − |
| glucose | + | + | + |
| α-Me-glucoside | + | + | − |
| glycerol | + | + | + |
| inositol | + | + | + |
| lactose | + | + | + |
| maltose | + | + | + |
| mannitol | + | + | + |
| mannose | + | + | + |
| melezitose | + | − | − |
| melibiose | + | − | + |
| raffinose | + | − | − |
| rhamnose | + | + | + |
| sorbitol | − | − | − |
| trehalose | + | + | + |
| xylose | + | + | + |
| control | − | − | − |
| Utilizes: | | | |
| benzoate | − | − | − |
| citrate | + | + | + |
| mucate | − | − | − |
| succinate | + | + | + |
| tartrate | − | − | − |
| control | − | − | − |
| Resistance to: | | | |
| bacitracin (10 units) | + | − | − |
| cephalothin (30 μg) | + | + | + |
| gentamicin (10 μg) | + | − | − |
| lincomycin (2 μg) | + | + | + |
| neomycin (30 μg) | − | − | − |
| oleandoinycin (15 μg) | + | − | − |
| penicillin G (10 units) | + | + | + |
| rifampin (5 μg) | − | − | − |
| streptomycin (10 μg) | + | + | − |
| tetracycline (30 μg) | − | − | − |
| tobramycin (10 μg) | + | + | − |
| vancomycin (30 μg) | + | + | − |
| chloramphenicol (30 μg) | − | − | − |
| erythromycin (15 μg) | + | − | − |
| nalidixic acid (30 μg) | + | + | − |
| novobiocin (30 μg) | − | + | − |
| polymixin B (300 units) | + | + | + |
| trimethoprim (5 μg) | + | + | + |

[a]+ = strain has the property;
− = strain does not have the property

Similarity coefficients were again calculated using a larger number of unit characters. The results are summarized in Table IV.

TABLE IV

Similarity Coefficient for A82846,
*Nocardia orientalis* and *Nocardia aerocolonigenes*

| Culture | Similarity Coefficient | |
|---|---|---|
| | Ssm | Sj |
| A82846 | 100 | 100 |
| N. orientalis | 81 | 76 |
| N. aerocolonigenes | 73 | 65 |

Neither *N. orientalis* nor *N. aerocolonigenes* has mycolic acids in its cell wall. Gordon, supra, describes three key properties to help distinguish *N. orientalis* from *N. aerocolonigenes*. Comparison of A82846 with the Nocardia species using Gordon's key properties is shown in Table V.

TABLE V

Comparison of Key Properties of A82846,
*Nocardia orientalis* and *Nocardia aerocolonigenes*

| Culture | Property | | |
|---|---|---|---|
| | Produces Acid From | | Resistance |
| | Erythritol | Me-α-glucoside | to Lysozyme |
| A82846 | − | + | + |
| N. orientalis | + | + | − |
| N. aerocolonigenes | − | − | + |

Although A82846 does not identically match the key properties of either Nocardia strain, it has a greater affinity to *N. orientalis* in cultural characteristics and a high similarity coefficient with *N. orientalis*. It also resembles *N. orientalis* in that it produces a glycopeptide antibiotic. A82846 is, therefore, classified as a strain of *Nocardia orientalis* (Pittenger and Brigham, 1956) Pridham and Lyons 1969. Because *N. orientalis* is recognized in the Approved Lists of Bacterial Names, supra, it is a validly published species.

Culture A82846.1 is a chemically induced mutant of the A82846 culture. The features in which A82846.1 differs from A82846 are shown in Table VI.

TABLE VI

Comparison of Differencies between A82846 and A82846.1

| Property | A82846 | A82846.1 |
|---|---|---|
| Fragmentation | minimal | abundant |
| Colony size | 7 mm | 5 mm |
| Colony surface | hard | soft |
| Aerial hyphae | abundant | trace |
| Reverse color | dark brown | light brown |
| Soluble pigment | + | − |
| Produces acid from: | | |
| ethanol | + | − |
| glycogen | + | − |
| melezitose | + | − |
| raffinose | + | − |
| salicin | + | − |
| Utilizes: | | |
| α-Me-glucoside | + | − |
| glycogen | + | − |
| melezitose | + | − |
| sorbose | + | − |
| butyrate | − | + |
| Melanoid pigments | + | − |

A82846.1 also differs from A82846 in the amount of antibiotic activity it produces. The other most apparent differences between the strains are that, unlike A82846, A82846.1 does not produce aerial mycelia and a distinctive soluble pigment.

Culture A82846.2 is a natural variant of culture A82846. Thus, the identifying characteristics of A82846.2 are essentially the same as those of A82846. The main difference between A82846 and A82846.2 is that the A82846.2 culture produces significantly greater amounts of antibiotic A82846 when grown in shake flasks than the A82846 culture does.

As is the case with other organisms, the characteristics of the A82846-producing cultures of this invention, *Nocardia orientalis* strains NRRL 18098, NRRL 18099 and NRRL 18100, are subject to variation. Thus, progeny of these strains, e.g., recombinants, mutants and variants, may be obtained by methods known in the art. For example, variants can be obtained by natural selection and mutants can be obtained by treatment with various known physical and chemical mutagens such as ultraviolet light, X rays, gamma rays and chemicals such as N-methyl-N'-nitro-N-nitrosoguanidine.

Recombinant strains can be developed by transforming the *Nocardia orientalis* strains, using procedures well known in the art. Because of the similarity between Nocardia and Streptomyces, transformation techniques and recombinant vectors developed for use with Streptomyces can also be used to transform Nocardia strains. Through the use of recombinant technology, the *Nocardia orientalis* strains can be transformed to express a variety of gene products in addition to the antibiotics these strains produce. For instance, one can transform the strains with a recombinant vector that confers resistance to an antibiotic to which the strains are normally sensitive. Transformants thus obtained will produce not only the A82846 antibiotics but also the resistance-conferring enzyme that allows selection of the transformed from wild-type cells. Furthermore, using similar techniques, one can modify the present strains to introduce multiple copies of the endogenous antibiotic-biosynthesis genes to achieve greater antibiotic yield. Progeny, i.e. natural and induced variants, mutants and recombinants, of the *Nocardia orientalis* strains NRRL 18098, NRRL 18099 and NRRL 18100 which retain the characteristic of A82846 production are part of this invention.

The culture medium used to grow the *Nocardia orientalis* cultures can be any one of a number of media. For economy in production, optimal yield, and ease of product isolation, however, certain culture media are preferred. Thus, for example, preferred carbohydrate sources in large-scale fermentation are glucose and potato dextrin, although ribose, xylose, fructose, galactose, mannose, mannitol, soluble starch and the like can also be used.

Preferred nitrogen sources are enzyme-hydrolyzed casein and meat peptones, although yeast extract, acid-hydrolyzed casein, beef extract, fish meal, liver meal, and the like can also be used.

Among the nutrient inorganic salts which can be incorporated in the culture media are the customary soluble salts capable of yielding zinc, sodium, magnesium, calcium, ammonium, chloride, carbonate, sulfate, nitrate and like ions.

Essential trace elements necessary for the growth and development of the organism should also be included in the culture medium. Such trace elements commonly occur as impurities in other substituents of the medium in amounts sufficient to meet the growth requirements of the organism. If foaming is a problem, small amounts (i.e. 0.2 ml/L) of an antifoam agent such as polypropylene glycol may be added to large scale fermentation media.

For production of substantial quantities of the A82846 antibiotics, submerged aerobic fermentation in tanks is preferred. Small quantities of the antibiotics may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank. The vegetative inoculum medium can be the same as that used for larger fermentations, but other media are also suitable.

The A82846 antibiotics are produced by the A82846-producing organisms when grown at temperatures between about 23° and about 37° C. Optimum temperatures for A82846 production appears to be about 30°–31° C.

As is customary in submerged aerobic culture processes, sterile air is blown into the vessel from the bottom while the medium is stirred with conventional turbine impellers. The maximum oxygen uptake of the fermentation under the conditions used thus far has not exceeded about 0.2 mM/L/minute. In general, the aeration rate and agitation rate should be sufficient to maintain the level of dissolved oxygen at or above 50% of saturation.

Production of the A82846 antibiotics can be followed during the fermentation by testing samples of the broth for antibiotic activity against organisms known to be sensitive to the antibiotic. One useful assay organism is *Bacillus subtilis* ATCC 6633. The bioassay is conveniently performed by the agar-well plate test.

Following their production under submerged aerobic fermentation conditions, the A82846 antibiotics can be recovered from the fermentation medium by methods used in the art. The antibiotic activity produced during fermentation of the A82846-producing organisms occurs in both the mycelia and the broth. Maximum recovery of A82846 is accomplished, therefore, by initially adjusting the pH to 10.5 to release A82846 from the mycelia and filtering the medium to separate the broth from the mycelial mass.

A82846 can be recovered from the filtered broth by a variety of techniques. A preferred technique involves adjusting the filtered broth to a pH of about 7 and adsorbing it onto a cation exchange resin, e.g. Dowex XF5-43278, Dowex-50 or Amberlite IR-120. The active material is eluted from the resin with a suitable solvent such as, for example, dilute $NH_4OH$ solution. The active fractions are then concentrated under vacuum, adsorbed on a macroreticular resin, e.g. Diaion HP-20 and Amberlite XAD-4, and eluted with a suitable solvent, such as water:isopropanol (95:5) containing 1% acetic acid, to give A82846. The active material can also be eluted with water:acetonitrile or water:methanol mixtures containing small amounts of acid.

A82846 can be separated into individual components A82846A, A82846B and A82846C by similar procedures. A preferred separation procedure involves reverse-phase silica-gel ($C_{18}$ or $C_8$) chromatography.

Alternatively, the culture solids, including medium constituents and mycelium can be used without extraction or separation, but preferably after removal of water, as a source of A82846. For example, after production of A82846, the whole fermentation broth can be dried by lyophilization, by drum-drying, or by azeotropic distillation and drying. The dried broth is then mixed directly into feed premix.

The A82846 antibiotics have excellent in vitro and in vivo activity against Gram-positive pathogenic bacteria. A particularly unexpected attribute of these antibiotics is their long serum half-life. For example, when administered intravenously to rats, vancomycin had a serum half-life of 45 minutes, whereas A82846A and A82846B each had a half-life of 2.2 hours.

The minimal inhibitory concentrations (MIC's) at which the A82846 antibiotics inhibit certain bacteria are given in Tables VII and VIII. The MIC's in Tables VII and VIII were determined by standard agar-dilution assays.

TABLE VII

In Vitro Antibacterial Activity of the A82846 Antibiotics

| | MIC (mcg/mL) | | |
|---|---|---|---|
| Test Organism | A82846A | A82846B | A82846C |
| Staphylococcus aureus X1.1 | 0.125 | 0.125 | 1 |
| Staphylococcus aureus V41[a] | 0.125 | 0.125 | 1 |
| Staphylococcus aureus X400[b] | 0.125 | 0.125 | 1 |
| Staphylococcus aureus S13E | 0.125 | 0.125 | 1 |
| Staphylococcus epidermidis 270 | 0.25 | 0.25 | 1 |
| Staphylococcus epidermidis 222 | 0.25 | 0.25 | 1 |
| Streptococcus pyogenes C203 | 0.125 | 0.125 | 1 |
| Streptococcus pneumoniae Park I | 0.125 | 0.125 | 2 |
| Streptococcus Group D X66 | 0.25 | 0.25 | 2 |
| Streptococcus Group D 2041 | 0.5 | 0.5 | 4 |
| Haemophilus influenzae C.L.[c] | —[e] | — | — |
| Haemophilus influenzae 76[d] | — | — | — |
| Escherichia coli EC14 | — | — | — |
| Klebsiella pneumoniae X26 | — | — | — |
| Pseudomonas aeruginosa X239 | — | — | — |

[a]Penicillin-resistant strain;
[b]Methicillin-resistant strain;
[c]Ampicillin-sensitive strain;
[d]Ampicillin-resistant strain;
[e]— = Not active at 128 mcg/mL, the highest level tested

TABLE VIII

In Vitro Activities of A82864A, A82864B and Vancomycin

| | No. of strains | MIC (mcg/mL) | | |
|---|---|---|---|---|
| Organism | Tested | A82846A | A82846B | Vancomycin |
| Staphylococcus aureus | 20 | 0.125–1.0 | 0.25–1.0 | 0.5–2.0 |
| Staphylococcus epidermidis | 20 | 0.25–2.0 | 0.5–1.0 | 1.0–2.0 |
| Streptococcus pyogenes | 12 | 0.125–0.25 | 0.125–0.25 | 0.5 |
| Streptococcus pneumoniae | 20 | ≦0.015–0.25 | 0.125–0.25 | ≦0.015–4.0 |
| Streptococcus sp. group. D | 20 | 0.25–1.0 | 0.25–1.0 | 1.0–2.0 |
| Streptococcus salivaris | 1 | 1.0 | 0.25 | 0.5 |

TABLE VIII-continued

In Vitro Activities of A82864A, A82864B and Vancomycin

| Organism | No. of strains Tested | MIC (mcg/mL) | | |
|---|---|---|---|---|
| | | A82846A | A82846B | Vancomycin |
| Streptococcus sanguis | 4 | 0.25–0.5 | 0.25 | 0.5–1.0 |
| Streptococcus mutans | 2 | 0.125–0.5 | 0.125–1.0 | 0.125–2.0 |

One important aspect of the antimicrobial activity of A82846 compounds is their activity against anaerobic bacteria. This activity is illustrated in Table IX, which summarizes the activity of A82846A and A82846B against various anaerobic bacteria, as determined by standard agar-dilution assay. End points were read after 24-hour incubation.

TABLE IX

Activity of A82846A and B Against Anaerobic Bacteria

| Anaerobic Bacteria | No. of Strains Tested | MIC (mcg/mL) | | |
|---|---|---|---|---|
| | | A82846A | A82846B | Vancomycin |
| Gram-positive Strains: | | | | |
| Clostridium difficile | 19 | 0.125–1 | ≦0.06–0.125 | 0.5–4 |
| Clostridium perfringens | 1 | ≦0.25 | 0.5 | 2 |
| Clostridium septicum | 1 | 0.5 | 0.5 | 2 |
| Eubacterium aerofaciens | 1 | ≦0.25 | 0.5 | 2 |
| Peptococcus asaccharolyticus | 3 | ≦0.25 | 0.06–0.5 | 1 |
| Peptococcus prevoti | 4 | 1–2 | 1–4 | 1–4 |
| Peptococcus variabilis | 1 | 0.5 | 1 | 1 |
| Peptococcus constellatus | 1 | 0.25 | 0.25 | 1 |
| Peptococcus magnus | 3 | 0.06–0.125 | 0.125–0.25 | 0.25–1 |
| Peptostreptococcus anaerobius | 8 | 0.06–2 | 0.06–8 | 0.25–2 |
| Peptostreptococcus intermedius | 3 | ≦0.25 | 0.25–0.5 | 0.5–1 |
| Propionibacterium acnes | 19 | ≦0.25 | ≦0.25 | 2–16 |
| Gram-negative Strains: | | | | |
| Bacteroides fragilis | 3 | >128 | >128 | 32–64 |
| Bacteroides thetaiotaomicron | 1 | 128 | 128 | 64 |
| Bacteroides melaninogenicus | 2 | >128 | >128 | >128 |
| Bacteroides vulgatis | 1 | 128 | >128 | 64 |
| Bacteroides corrodens | 1 | >128 | >128 | 64 |
| Fusobacterium symbiosum | 1 | 128 | 128 | 4 |
| Fusobacterium necrophorum | 1 | 128 | 128 | 1 |

The A82846 antibiotics have also shown in vivo antimicrobial activity against experimentally-induced infections in laboratory animals. When two doses of test compound were administered to mice experimentally infected with the test organism, the activity observed was measured as an $ED_{50}$ value [effective dose in mg/kg to protect 50% of the test animals: see Warren Wick, et al., *J. Bacteriol.* 81, 233–235 (1961)]. $ED_{50}$ values observed for illustrative compounds are given in Table X.

TABLE X

In Vivo Activity of A82846 Antibiotics

| Compound | $ED_{50}$ Value[a] | | |
|---|---|---|---|
| | Staphylococcus aureus | Streptococcus pyogenes | Streptococcus pneumoniae |
| A82846A | 0.19 | 0.19 | 0.17 |
| A82846B | 0.19 | 0.20 | 0.18 |
| A82846C | 2.18 | 2.71 | 5.87 |
| Vancomycin | 1.3 | 0.72 | 1.52 |

[a]mg/kg × 2; doses administered subcutaneously to mice 1 and 4 hours post-infection In one important aspect of their antibacterial activity, the A82846 antibiotics are useful for treating pyelonephritis. For example, A82846A and A82846B were more effective than vancomycin in affording protection in an experimental descending pyelonephritis infection in rats. This test was carried out using a procedure like that described in U.S. Pat. No. 4,208,403. The results observed are summarized in Table XI.

TABLE XI

Activity of A82846A and B in the Rat Descending Pyelonephritis Test

| Compound | Dosage (mg/kg × 12)[a] | Percent of Rats Cured | Percent of Rats with a 4-Log Reduction in Titer |
|---|---|---|---|
| A82846A | 10 | 88 | 100 |
| | 5 | 75 | 88 |
| | 2 | 63 | 100 |
| A82846B | 10 | 100 | 100 |
| | 5 | 100 | 100 |
| | 2 | 50 | 88 |
| Vancomycin | 10 | 63 | 100 |
| | 5 | 38 | 88 |
| | 2 | 38 | 75 |

[a]Doses twice per day subcutaneously for 6 days

The A82846 antibiotics are also useful in the treatment of endocarditis. For example, A82846A and B were as effective as vancomycin in treating an experimental catheter-induced endocarditis infection in rats. In this test, rats were prepared by inserting a plastic catheter into the right carotid artery, feeding it down into the right ventricle of the heart and anchoring it securely. The animals were allowed to rest two days, and then the test organism, *Streptococcus faecalis* X-66, was administered intravenously. The organism titer was approximately $5 \times 10^8$/mL; 0.5 mL was administered.

The compounds were administered subcutaneously 15 minutes prior to infection and at 12-hour intervals for 14 days, a total of 28 treatments. The animals were held 2 days after therapy; then, the hearts were removed, homogenized, diluted and plated on trypticase soy agar. Plates were incubated 48 hours before counting.

The results of these studies are summarized in Table XII.

TABLE XII

Activity of A82846A and B in the Rat Endocarditis Test[a]

| Compound | Dosage[b] (mg/kg × 28) | 16 Days | |
|---|---|---|---|
| | | % Cured | % With 4 Log Drop[c] |
| A82846A | 20 | 100 | 100 |
| A82846B | 20 | 100 | 100 |
| Vancomycin | 20 | 100 | 100 |

[a]Catheter-induced endocarditis using *Streptococcus faecalis* X-66
[b]Subcutaneous doses at 12-hour intervals for 14 days
[c]% of animals sacrificed with 4 log drop Pharmaceutical formulations of the A82846 antibiotics are also part of this invention. Thus, the antibiotic, preferably in the form of a pharmaceutically acceptable salt, can be formulated for oral or parenteral administration for the therapeutic or prophylactic treatment of bacterial infections. For example, the compound can be admixed with conventional pharmaceutical carriers and excipients and used in the form of tablets, capsules, elixirs, suspensions, syrups, wafers and the like. The compositions comprising an A82846 antibiotic will contain from about 0.1 to about 90% by weight of the active compound, and more generally from about 10 to about 30%. The compositions may contain common carriers and excipients, such as corn starch or gelatin, lactose, sucrose, microcrystalline cellulose, kaolin, mannitol, dicalcium phosphate, sodium chloride and alginic acid. Disintegrators commonly used in the formulations of this invention include croscarmellose sodium, microcrystalline cellulose, corn starch, sodium starch glycolate and alginic acid. Tablet binders that can be included are acacia, methylcellulose, sodium carboxymethylcellulose, polyvinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica. Flavoring agents such as peppermint, oil of wintergreen, cherry flavoring or the like can also be used. It may be desirable to add a coloring agent to make the dosage form more esthetic in appearance or to help identify the product.

For intravenous (IV) use, a water soluble form of the antibiotic can be dissolved in one of the commonly used intravenous fluids and administered by infusion. Such fluids as, for example, physiological saline, Ringer's solution or 5% dextrose solution can be used.

For intramuscular preparations, a sterile formulation of a suitable soluble salt form of the compound, for example the hydrochloride salt, can be dissolved and administered in a pharmaceutical diluent such as Water-for-Injection, physiological saline or 5% glucose solution. A suitable insoluble form of the compound may be prepared and administered as a suspension in an aqueous base or a pharmaceutically acceptable oil base, e.g. an ester of a long chain fatty acid such as ethyl oleate.

For oral use, a sterile formulation of a suitable salt form of the antibiotic, for example, the hydrochloride salt, formulated in a diluent such as distilled or deionized water, is particularly useful.

Alternatively, the unit dosage form of the antibiotic can be a solution of the antibiotic, preferably in its salt form, in a suitable diluent in sterile, hermetically sealed ampoules. The concentration of the antibiotic in the unit dosage may vary, e.g. from about 1 percent to about 50 percent depending on the particular form of the antibiotic and its solubility and the dose desired by the physician.

In a further aspect, this invention provides a method for treating infectious diseases, especially those caused by Gram-positive microorganisms, in animals. The animal may be either susceptible to, or infected with, the microorganism. The method comprises administering to the animal an amount of an A82846 antibiotic which is effective for this purpose. In general, an effective amount of A82846 antibiotic is a dose between about 0.5 and about 100 mg/kg. A preferred dose is from about 1 to about 60 mg/kg of active compound. A typical daily dose for an adult human is from about 50 mg to about 1.0 g.

In practicing this method, the antibiotic can be administered in a single daily dose or in multiple doses per day. The treatment regime may require administration over extended periods of time, e.g., for several days or for from one to six weeks. The amount per administered dose or the total amount administered will depend on such factors as the nature and severity of the infection, the age and general health of the patient, the tolerance of the patient to the antibiotic and the microorganism or microorganisms involved in the infection.

A convenient method of practicing the treatment method is to administer the antibiotic via IV infusion. In this procedure a sterile formulation of a suitable soluble salt of the antibiotic is incorporated in a physiological fluid, such as 5% dextrose solution, and the resulting solution is infused slowly IV. Alternatively, the piggy-back method of IV infusion can also be used.

In other embodiments, this invention relates to 1) methods of increasing feed-utilization efficiency in animals such as poultry, swine, sheep and cattle, 2) methods of promoting growth in animals such as poultry, swine, sheep and cattle raised for meat production and 3) methods of enhancing milk production in lactating ruminants. For increasing feed-utilization efficiency and promoting growth, an A82846 antibiotic is administered orally in a suitable feed in an amount of from about 2 to about 200 grams per ton of total feed. For beef cattle, for example, a range of about 12 to 3000 mg/head/day is suitable. For enhancing milk production in lactating ruminants, oral administration of a daily amount of from about 0.04 to about 16 mg/kg of body weight (or about 25 to about 5000 mg/animal/day) is suggested.

In order to illustrate more fully the operation of this invention, the following examples are provided:

EXAMPLE 1

A82846 HPLC Assay Method

The following analytical HPLC systems are useful for the A82846 components:
1. Cation Exchange Resin Column
   Column Support: Zorbax* SCX(4.6×150 mm)
   System: Gradient Elution A:B (4:1) to A:B (1:9) in 5 min., hold for 15 min.
   A=MeOH:0.1M $NaH_2PO_4$ (1:9)
   B=MeOH:0.9M $NaH_2PO_4$ (1:9)
   Flow Rate: 1.0 mL/min
   Detection: UV at 225 nm
   Retention Times: are concentration dependent, but are approximately:
   A82846C=6.6 min
   A82846B=8.9 min
   A82846A=9.5 min 2. Reverse Phase Column Column Support: Zorbax* ODS (4.6×150 mm)

System: Gradient Elution 1% $(NH_4)H_2PO_4$:$CH_3CN$ (95:5) to (1:1) in 20 min.

Flow Rate: 1.0 mL/min

Detection: UV at 225 nm

Retention Times: A82846A=7.3 min
A82846C=7.6 min
A82846B=8.0 min

*Zorbax columns are products of E. I. duPont de Nemours & Co., Inc., Wilmington, Del. 19898

EXAMPLE 2

Preparation of Antibiotic A82846 Using Culture A82846

A. Shake-flask Fermentation of Culture A82846

The culture *Nocardia orientalis* NRRL 18098, either as a lyophilized pellet or as a suspension maintained in liquid nitrogen, is used to inoculate a seed medium having the following composition:

| SEED MEDIUM | |
|---|---|
| Ingredient | Amount (%) |
| Glucose | 1.0 |
| Soluble starch | 2.0 |
| Yeast extract | 0.5 |
| Enzymatic hydrolysate of casein* | 0.5 |
| CaCO$_3$ | 0.1 |
| Deionized water | q.s. 1 liter |

Adjust the pH of the medium to about 7.5 with NaOH before sterilizing.
*NZ Amine A, Sheffield Chemical Co., Norwich, NY Slants or plates are prepared by adding 2.5% agar to the seed medium. The inoculated slant is incubated at 30° C. for from about 10 to about 14 days. The mature slant culture is scraped with a sterile tool to loosen the spores and remove and mascerate the mycelial mat. About one-fourth of the loosened spores and culture growth thus obtained is used to inoculate 50 mL of a first-stage seed medium.

The inoculated first-stage medium is incubated in a 250-mL Erlenmeyer flask at 30° C. for about 24–48 hours on a shaker orbiting in a two-inch (5.08 cm) circle at 250 rpm.

This incubated first-stage medium (0.5 mL) is used to inoculate 50 mL of a production medium having the following composition:

| Ingredient | Amount (%) |
|---|---|
| Glucose | 2.5 |
| Soybean flour | 1.5 |
| Potato dextrin | 3.0 |
| CaCO$_3$ | 0.25 |
| Blackstrap molasses | 0.3 |
| Acid-hydrolyzed casein* | 0.5 |
| Deionized water | q.s. 1 liter |

(Presterilization pH adjusted to 7.5 with NaOH)
*Hy-Case, Sheffield Chemical Co.

The inoculated production medium is incubated in a 250-mL wide-mouth Erlenmeyer flask at 30° C. for 4 to 5 days on a shaker orbiting in a two-inch circle at 250 rpm.

B. Tank Fermentation of Culture A82846

In order to provide a larger volume of inoculum, 10 mL of incubated first-stage medium, prepared as described in Section A, is used to inoculate 400 mL of a second-stage growth medium having the same composition as that of the first-stage medium. This second-stage vegetative medium is incubated in a 2-L wide-mouth Erlenmeyer flask for about 48 hours at 30° C. on a shaker orbiting in a two-inch circle at 250 rpm.

Incubated second-stage vegetative medium (1000 mL) thus prepared is used to inoculate 100 liters of sterile production medium, prepared as described in Section A except that P-2000 antifoam (0.3 g/L) is added. The inoculated production medium is allowed to ferment in a 165-L stirred fermentation tank for 90 to 100 hours at a temperature of 30° C. The airflow in the stirred vessel (80 RPM) is adjusted to maintain a dissolved oxygen level above 50% of air saturation.

C. Alternate Tank Fermentation of Culture A82846

The procedure of Section B is followed except that an appropriate amount of vegetative medium is used to inoculate approximately 1200 gallons of production medium in a 1600-gallon (4536-L) fermentation tank.

EXAMPLE 3

Preparation of Antibiotic A82846 Using Culture A82846.1

The culture *Nocardia orientalis* NRRL 18099, either as a lyophilized pellet or as a suspension maintained in liquid nitrogen, is cultured using the procedure described in Example 2 except that the production medium has the following composition:

| Ingredient | Amount (%) |
|---|---|
| Glucose | 1.0 |
| Potato dextrin | 2.0 |
| Peptone* | 1.0 |
| CaCO$_3$ | 0.2 |
| Blackstrap molasses | 2.0 |
| Deionized water | q.s. 1 liter |
| No pH adjustment | |

*Bactopeptone (Difco Laboratories)

EXAMPLE 4

Preparation of Antibiotic A82846 Using Culture A82846.2

The culture *Nocardia orientalis* NRRL 18100, either as a lyophilized pellet or as a suspension maintained in liquid nitrogen, is cultured using the procedure described in Example 2 except that the acid-hydrolyzed casein used is Amicase (Sheffield Chemical Co.).

EXAMPLE 5

Preparation of Crude A82846

Fermentation broth (4200 L) from a 1600-gallon fermenter, prepared as described in Example 2, Section C, was adjusted to pH 10.5 with 5N NaOH, and 3% Celite 545 (filter aid) was added. The mixture was filtered through a filter press, and the press was washed with water. The combined filtrate and wash (4200 L) was adjusted to pH 7 with 5N HCl (or $H_2SO_4$) and applied to a column of Dowex-XFS-43278 ($NH_4$+) resin (200 L filtrate/10 L resin). The column was eluted at a flow rate of 750 mL/min. Fractions were assayed either by bioassay using *Bacillus subtilis* or HPLC.

The column was washed with 5 column volumes of water, collecting 100-L aliquots.

The active material was eluted from the resin with 5 column volumes of 0.05N $NH_4OH$, collecting 25-L fractions. Fractions containing A82846 were combined and concentrated in vacuo to a volume of about 30 L. This solution was applied to a 10-L column of Diaion HP-20 resin in water. The column was washed with 3 column volumes of water at a flow rate of 300 mL/min. The water wash was discarded. The active material was eluted from the column with a solution of $H_2O$:iPrOH (95:5) containing 1.0% acetic acid at a rate of 100 mL/min, collecting 4-L fractions and assaying by bioassay and HPLC. Fractions containing A82846 (#6–14) were combined, concentrated in vacuo and freeze-dried to yield 356 g of crude A82846.

EXAMPLE 6

Isolation of A82846A and A82846B

A. Separation of Enriched A82846A and A82846B

A82846 (30 g), prepared as described in Example 5, was dissolved in water (500 mL) and applied to a pressurized 30-L stainless-steel column of silica gel LP-1/$C_{18}$ equilibrated in 1% $NH_4H_2PO_4$. The column was developed using a gradient of 1% $NH_4H_2PO_4$ (60 L) to water:acetonitrile (88:12) containing 1% $NH_4H_2PO_4$ (60 L) at a flow rate of 250–300 mL/min (max pressure of 600 psi), collecting 4-L fractions and monitoring elution using a UV detector at 254 nm. Individual fractions were assayed by analytical HPLC. Fractions rich in A82846A (#6–9) and fractions rich in A82846B (#10–17) were each combined and concentrated in vacuo.

B. Purification of A82846A

A82846A-rich concentrates from two 30-g runs carried out as described in Sect. A were desalted on a 1750-mL column of Diaion HP-20 SS, washing with water, eluting with $H_2O$:iPrOH (95:5) containing 0.5% acetic acid and assaying by analytical HPLC. Fractions containing A82846A were combined, concentrated and freeze-dried to yield 7.4 g of A82846A-enriched preparation.

The A82846A-enriched preparation (7.2 g) was dissolved in water and applied to a preparative HPLC column of silica gel LP-1/$C_{18}$ in 1% $(NH_4)H_2PO_4$. The column was developed with a gradient of 1% $(NH_4)H_2PO_4$ to 1% $(NH_4)H_2PO_4$:acetonitrile (9:1), monitoring the elution by analytical HPLC at 254 nm and eluting at a flow rate of 48 mL/min. After the first 10 L was eluted, 500-mL fractions were collected.

Fractions containing A82846A (#4–10) and fractions containing A82846B (#12–20) were each combined and concentrated in vacuo. Concentrates of A82846A from 3 runs were combined and applied to a 1750-mL column of Diaion HP-20 SS to desalt the solution. The column was washed with water, and A82846A was eluted with $H_2O$:iPrOH (95:5) containing 0.5% acetic acid. Elution was monitored by HPLC. Fractions containing A82846A were combined, concentrated and freeze-dried to yield 7.9 g of purified A82846A.

C. Purification of A82846B

A82846B-enriched fractions from 3 preparative HPLC runs separating A82846A and A82846B, obtained as described in Section B, were combined and desalted on a 1750-mL column of Diaion HP-20 SS, washing with water and eluting with $H_2O$:iPrOH (95:5) containing 0.5% acetic acid. Elution was monitored by HPLC and the A82846B fractions were combined, concentrated in vacuo and freeze-dried to yield 8.8 g of purified A82846B.

D. Desalting

Desalting can also be accomplished using Diaion HP-20 resin and eluting with MeOH:$H_2O$ (4:1) containing 0.1% acetic acid.

EXAMPLE 7

Isolation of A82846C

A. Separation of A82846

Fermentation broth (461 L), obtained from four 165-L fermentations carried out as described in Example 2, Section B, was adjusted to pH 10.5 with 5N NaOH and filtered with 3% Hyflo Supercel filter aid. The filtrate (430 L) was adjusted to pH 7 with 5N HCl and applied to a column containing 10 L of Dowex-XFS-43278 ($NH_4^+$) resin. The column was washed with 50 L of water, and the active material was eluted with 0.05N $NH_4OH$ (50 L), collecting 4-L fractions. Elution was monitored by bioassay. Active fractions (#1–7) were combined, concentrated in vacuo to a volume of about 1700 mL and freeze-dried to yield 283.9 g of crude A82846.

B. Separation of A82846A, B and C

Crude A82846 (2 g), obtained as described in Section A, was dissolved in water and applied to a 2"×45" stainless-steel preparative HPLC column containing 2110 mL of silica gel LP-1/$C_{18}$ resin in 1% $(NH_4)H_2PO_4$. The column was developed using a gradient of from 1% $(NH_4)H_2PO_4$ to 1% $(NH_4)H_2PO_4$:acetonitrile (92:8) at a flow rate of 70 mL/min. collecting 400-mL fractions and monitoring by UV at 254 mm.

Fractions containing A82846A (#11–14) were combined as pool 1; fractions containing A82846C (#16–20) were combined as pool 2; and fractions containing A82846B (#21–25) were combined as pool 3.

C. Purification of A82846C

Pool 2 was concentrated to a volume of about 200 mL and applied to a 7-×45-cm glass column containing 1800 mL of Diaion HP-20 resin for desalting. The active material was eluted with MeOH:$H_2O$ (4:1) containing 0.1% acetic acid, collecting 1-L fractions at a flow rate of 25 mL/min. Fractions containing C (#9–12) were pooled, concentrated in vacuo and freeze-dried to give 662.2 mg of semi-purified A82846C.

The semi-purified A82846C (500 mg) was further purified by repeating the reverse-phase HPLC steps, using a 1"×48" steel column containing 450 mL of silica gel LP-1/$C_{18}$, a gradient of 1% $(NH_4)H_2PO_4$ to 1% $(NH_4)H_2PO_4$:acetonitrile (92:8), a flow rate of 11 mL/min, collecting 25-mL fractions and monitoring at 254 nm. Fractions containing A82846C (#169–210) were pooled and desalted on a 5-×45-cm glass column containing HP-20 resin. The column was eluted with MeOH:$H_2O$ (4:1) containing 0.1% acetic acid, collecting 100-mL fractions and following the elution by analytical HPLC with UV at 225 nm. Fractions containing A82846C (#5–11) were combined, concentrated in vacuo and freeze-dried to yield 127.3 mg of A82846C.

Pool 1 containing A82846A and pool 3 containing A82846B were purified in the same manner described for A82846C to obtain additional purified A82846A and A82846B.

D. Further Purification of A82846C

A82846C (70 mg) was purified further using the following preparative chromatographic procedure:

Column: Zorbax SCX (9.2×250 mm) cation exchange

Mobile Phase: A linear gradient starting from 0.15M $NaH_2PO_4$ buffer containing 10% MeOH to 0.9M $NaH_2PO_4$ buffer containing 10% MeOH in 6 min. and holding 5 min. (no adjustment made to the buffer).

Flow Rate: 6.0 mL/min.

Detection: UV at 280 nm

Load: 6.0 mg/injection in $H_2O$

A82846C was collected by use of an automated fraction collector (Gilson 201C) equipped with a peak detection mechanism. Mobile phase was delivered by a Millipore Waters M600 Gradient HPLC System, and sample solution was injected via a Hitachi autosampler.

Fractions containing A82846C were combined, concentrated to a volume of 30 mL and applied to an HP-20 column (50 mL). The column was washed with $H_2O$ and eluted with $H_2O$:isopropanol (95:5) containing 0.5% HOAc, collecting 25 mL fractions. Fractions containing A82846C (#9–14) were combined, concentrated and lyophilized to yield 37 mg of purified A82846C.

EXAMPLE 8

Preparation of A82846 Salts

Procedure:

In each case, the A82846 component (100 mg) was dissolved in deionized water (10 mL). The pH of this solution was adjusted to about pH 3, using 0.5N acid (HCl, $H_2SO_4$ and $H_3PO_4$). The solution was lyophilized to give the appropriate salt form. It is important to note that if the pH is lowered to much below pH 3 (i.e. pH 2), the component is degraded. The following yields were obtained:

| Salt | Yield (mg) | |
|---|---|---|
| | A82846A | A82846B |
| HCl | 93.8 | 88.1 |
| $H_2SO_4$ | 92.5 | 75.4 |
| $H_3PO_4$ | 110.8 | 105.7 |

EXAMPLE 9

A82846A Tablet Formulation

Tablets containing A82846A can be prepared using the following ingredients and amounts:

| Ingredient | Weight |
|---|---|
| A82846A phosphate | 282.9 mg |
| Microcrystalline cellulose | 101.1 mg |
| Croscarmellose sodium | 12.0 mg |
| Providone | 12.0 mg |
| Magnesium stearate | 3.0 mg |
| Stearic acid | 4.0 mg |
| Purified water | 0.16 mL |

Add A82846A phosphate, a portion of the microcrystalline cellulose and a portion of the croscarmellose sodium to a suitable container and blend until homogenous. Prepare a solution of Povidone in water, and add the Povidone solution to the blended powders. Granulate the resulting mixture, size if necessary and dry. Add the remaining microcrystalline cellulose and croscarmellose sodium to the dried mixture and blend. Add magnesium stearate and stearic acid, and blend the mixture. Compress the resulting powder blend into tablets.

EXAMPLE 10

A82846B Capsule Formulation

Capsules containing A82846B can be prepared using the following ingredients and amounts:

| Ingredient | Weight |
|---|---|
| A82846B hydrochloride | 262.2 mg |
| Corn starch flowable powder | 137.7 mg |
| Silicone fluid 350 centistokes | 2.7 mg |
| Corn starch | 147.1 mg |

Blend A82846B hydrochloride, starch flowable powder, silicone fluid 350 centistokes and starch powder in a suitable mixer until homogeneous. Fill into appropriate size hard gelatin capsules.

EXAMPLE 11

A82846A Suspension Formulation

Prepare a sterile insoluble form of A82846A by crystallization or precipitation. Mill or screen to a particle size suitable for suspension. Suspend the A82846A in the following vehicle.

| Ingredient | Amount |
|---|---|
| Lecithin | 1% |
| Sodium citrate | 2% |
| Propylparaben | 0.015% |
| Water for Injection | q.s. to desired volume |

The suspension may be manufactured in bulk and filled into vials or may be prepared extemporaneously by adding the vehicle to the A82846A in the vial.

We claim:

1. Antibiotic A82846A, which has the following characteristics:

Molecular Weight: 1556

Empirical Formula: $C_{73}H_{89}N_{10}O_{26}Cl$

FAB-MS (thioglycerol): FIG. 4

UV ($H_2O$) $\lambda$max: 281 nm ($\epsilon$ 5,052)

IR (KBr): FIG. 1

NMR [$(CD_3)_2SO$]: FIG. 7 pKa ($H_2O$): 4.7, 9.5

(66% DMF): 5.5, 6.8, 7.9, 9.4, 12.3

Contains: aspartic acid and 4-epi-vancosamine; or a salt thereof.

2. A compound of claim 1 which is Antibiotic A82846A or a pharmaceutically acceptable salt thereof.

3. A composition for treating Gram-positive bacterial infections comprising an effective antibacterial amount of a compound of claim 2 and a suitable vehicle.

4. A method for treating infections caused by Gram-positive bacteria which comprises administering an effective amount of a compound of claim 2 to an animal.

5. A feed composition for increasing feed utilization efficiency in ruminant animals, for promoting growth in animals, or for improving milk production in lactating animals, comprising animal feed and an effective amount of a compound of claim 2.

6. A method for increasing feed-utilization efficiency in a ruminant animal which comprises orally administering an effective amount of a composition of claim 5 to the animal.

7. A method for promoting growth in an animal which comprises orally administering an effective amount of a composition of claim 5 to the animal.

8. A method for improving milk production in a lactating ruminant comprising orally administering an effective amount of a composition of claim 5 to the ruminant.

9. Antibiotic A82846A as claimed in claim 1 which is produced by culturing *Nocardia orientalis* NRRL 18098 or an A82846A-producing progeny thereof under submerged aerobic conditions in a suitable culture medium until a substantial amount of A82846A is produced.

10. Antibiotic A82846A as claimed in claim 1 which is produced by culturing *Nocardia orientalis* NRRL 18099 or an A82846A-producing progeny thereof under submerged aerobic conditions in a suitable culture medium until a substantial amount of A82846A is produced.

11. Antibiotic A82846A as claimed in claim 1 which is produced by culturing *Nocardia orientalis* NRRL 18100 or an A82846A-producing progeny thereof under submerged aerobic conditions in a suitable culture medium until a substantial amount of A82846A is produced.

12. Antibiotic A82846B, which has the following characteristics:

Molecular Weight: 1590

Empirical Formula: $C_{73}H_{88}N_{10}O_{26}Cl_2$

FAB-MS (thioglycerol): FIG. 5

UV ($H_2O$) λmax: 280 nm (ε 5,192)

IR (KBr): FIG. 2

NMR [$(CD_3)_2SO$]: FIG. 8 pKa ($H_2O$): 4.65, 9.5

Contains: aspartic acid and 4-epi-vancosamine; or a salt thereof.

13. A compound of claim 12 which is Antibiotic A82846B or a pharmaceutically acceptable salt thereof.

14. A composition for treating Gram-positive bacterial infections comprising an effective antibacterial amount of a compound of claim 13 and a suitable vehicle.

15. A method for treating infections caused by Gram-positive bacteria which comprises administering an effective amount of a compound of claim 13 to an animal.

16. A feed composition for increasing feed utilization efficiency in ruminant animals, for promoting growth in animals, or for improving milk production in lactating animals, comprising animal feed and an effective amount of a compound of claim 13.

17. A method for increasing feed-utilization efficiency in a ruminant animal which comprises orally administering an effective amount of a composition of claim 16 to the animal.

18. A method for promoting growth in an animal which comprises orally administering an effective amount of a composition of claim 16 to the animal.

19. A method for improving milk production in a lactating ruminant comprising orally administering an effective amount of a composition of claim 16 to the ruminant.

20. Antibiotic A82846B as claimed in claim 12 which is produced by culturing *Nocardia orientalis* NRRL 18098 or an A82846B-producing progeny thereof under submerged aerobic conditions in a suitable culture medium until a substantial amount of A82846B is produced.

21. Antibiotic A82846B as claimed in claim 12 which is produced by culturing *Nocardia orientalis* NRRL 18099 or an A82846B-producing progeny thereof under submerged aerobic conditions in a suitable culture medium until a substantial amount of A82846B is produced.

22. Antibiotic A82846B as claimed in claim 12 which is produced by culturing *Nocardia orientalis* NRRL 18100 or an A82846B-producing progeny thereof under submerged aerobic conditions in a suitable culture medium until a substantial amount of A82846B is produced.

23. Antibiotic A82846C, which has the following characteristics:

Molecular weight: 1522

Empirical Formula: $C_{73}H_{90}N_{10}O_{26}$

FAB-MS (thioglycerol): FIG. 6

UV ($H_2O$) λmax: 280 nm (ε 5,198)

IR (KBr): FIG. 3

NMR [$(CD_3)_2SO$]: FIG. 9 pKa ($H_2O$): 4.6, 9.4

Contains: aspartic acid and 4-epi-vancosamine; or a salt thereof.

24. A compound of claim 23 which is Antibiotic A82846C or a pharmaceutically acceptable salt thereof.

25. A composition for treating Gram-positive bacterial infections comprising an effective antibacterial amount of a compound of claim 24 and a suitable vehicle.

26. A method for treating infections caused by Gram-positive bacteria which comprises administering an effective amount of a compound of claim 24 to an animal.

27. A feed composition for increasing feed utilization efficiency in ruminant animals, for promoting growth in animals, or for improving milk production in lactating animals, comprising animal feed and an effective amount of a compound of claim 24.

28. A method for increasing feed-utilization efficiency in a ruminant animal which comprises orally administering an effective amount of a composition of claim 27 to the animal.

29. A method for promoting growth in an animal which comprises orally administering an effective amount of a composition of claim 27 to the animal.

30. A method for improving milk production in a lactating ruminant comprising orally administering an effective amount of a composition of claim 27 to the ruminant.

31. Antibiotic A82846C as claimed in claim 23 which is produced by culturing *Nocardia orientalis* NRRL 18098 or an A82846C-producing progeny thereof under submerged aerobic conditions in a suitable culture medium until a substantial amount of A82846C is produced.

32. Antibiotic A82846C as claimed in claim 23 which is produced by culturing *Nocardia orientalis* NRRL 18099 or an A82846C-producing progeny thereof under submerged aerobic conditions in a suitable culture medium until a substantial amount of A82846C is produced.

33. Antibiotic A82846C as claimed in claim 23 which is produced by culturing *Nocardia orientalis* NRRL 18100 or an A82846C-producing progeny thereof under submerged aerobic conditions in a suitable culture medium until a substantial amount of A82846C is produced.

* * * * *